(12) United States Patent
Kaneda

(10) Patent No.: US 8,282,617 B2
(45) Date of Patent: Oct. 9, 2012

(54) DISPOSABLE DIAPER

(75) Inventor: Masahiro Kaneda, Shikokuchuo (JP)

(73) Assignee: Daio Paper Corporation, Ehime (JP)

( * ) Notice: Subject to any disclaimer, the term of this patent is extended or adjusted under 35 U.S.C. 154(b) by 523 days.

(21) Appl. No.: 12/448,626

(22) PCT Filed: Dec. 28, 2007

(86) PCT No.: PCT/JP2007/075281
§ 371 (c)(1),
(2), (4) Date: Jun. 26, 2009

(87) PCT Pub. No.: WO2008/081930
PCT Pub. Date: Jul. 10, 2008

(65) Prior Publication Data
US 2009/0326504 A1 Dec. 31, 2009

(30) Foreign Application Priority Data

Dec. 28, 2006 (JP) .................................. 2006-356350
Jan. 31, 2007 (JP) .................................. 2007-022293

(51) Int. Cl.
*A61F 13/15* (2006.01)
(52) U.S. Cl. ............... 604/393; 604/385.27; 604/385.01
(58) Field of Classification Search .................. 604/367, 604/385.01, 385.03, 385.101, 385.16, 385.22, 604/385.24–385.27, 393
See application file for complete search history.

(56) References Cited

U.S. PATENT DOCUMENTS
2004/0243083 A1* 12/2004 Matsuda et al. ......... 604/385.01

FOREIGN PATENT DOCUMENTS

| JP | S63-177907 | 11/1988 |
|---|---|---|
| JP | H3-107920 | 11/1991 |
| JP | H10-96157 | 4/1998 |
| JP | H11-4852 | 1/1999 |
| JP | 2000-93462 | 4/2000 |
| JP | 2001-087312 | 4/2001 |
| JP | 2002-209942 | 7/2002 |
| JP | 2003-010244 | 1/2003 |
| JP | 2003-531644 | 10/2003 |
| JP | 2003-339751 | 12/2003 |
| JP | 2003-339768 | 12/2003 |

(Continued)

*Primary Examiner* — Michele M Kidwell
(74) *Attorney, Agent, or Firm* — DLA Piper LLP (US)

(57) ABSTRACT

[Problems] To improve the air permeability of a waist portion of a disposable diaper
[Means for Solving Problems] In an underpants type disposable diaper, including: a ventral-side outer sheet 12F and a back-side outer sheet 12B which are not connected but separated at a crotch portion; an absorber 20 having a liquid impervious sheet and a crotch outer sheet 12M laminated on an underside of the liquid impervious sheet in the absorber so as to be exposed on an external surface of a product, assuming that the number of sheets disposed on the underside of the liquid impervious sheet is B1 at the intermediate portion 23, A1 at front- and back-side outer overlap sections X and Z, and C1 at the front- and back-side outer nonoverlap sections 20F and 20B, there is established a relationship of B1<C1<A1.

11 Claims, 20 Drawing Sheets

FOREIGN PATENT DOCUMENTS

| | | |
|---|---|---|
| JP | 2004-249079 | 9/2004 |
| JP | 2004-329386 | 11/2004 |
| JP | 2004-350809 | 12/2004 |
| JP | 2005-027839 | 2/2005 |
| JP | 2005-118225 | 5/2005 |
| JP | 2005-204744 | 8/2005 |
| JP | 2006-6742 | 1/2006 |
| JP | 2006-217951 | 8/2006 |
| JP | 2008-508082 | 3/2008 |
| JP | 2008-515479 | 5/2008 |
| WO | WO 2004/037145 | 5/2004 |
| WO | WO 2004/062398 | 7/2004 |
| WO | WO 2005/089690 | 9/2005 |
| WO | WO 2006/017718 | 2/2006 |
| WO | WO 2006/093440 | 9/2006 |
| WO | WO 2006/118214 | 11/2006 |

* cited by examiner

DISPOSABLE DIAPER

TECHNICAL FIELD

The present invention relates to an underpants type disposable diaper with two separate ventral- and back-side outer sheets.

BACKGROUND ART

A general underpants type disposable diaper includes front and back body parts that are joined at both sides to form joined sections at both sides, an outer sheet with a waist opening and a pair of right and left leg openings, and an absorber that is fixed to an inner surface of the outer sheet along a central portion in the width direction in an area ranging from a ventral side through a crotch portion to a back side. Such an underpants type disposable diaper is attached to a wearer by inserting the legs of the wearer through the waist opening into the leg openings.

Other than such a diaper with a single-piece outer sheet, there has been proposed a two-separated type disposable diaper which has two separate ventral- and back-side outer sheets, the ventral- and back-side outer sheets being not connected but separated at the crotch portion (refer to Patent Document 1, for example). The two-separated disposable diaper has advantages that, at the time of manufacture, trims (unnecessary waste portions) can be reduced in punching out the leg openings, and materials for the ventral- and back-side outer sheets can be separately selected.

Meanwhile, an absorber in the two-separated disposable diaper includes a liquid pervious top sheet on a top side, a liquid impervious sheet on an underside, and an absorbent element interposed between the foregoing sheets to absorb and retain a liquid. The absorber is connected on the under surface at a front end portion to the ventral-side outer sheet on the inner surface at a central portion in the width direction, and is connected on the under surface at a back end portion to the back-side outer sheet on the inner surface at a central portion in the width direction. The absorber is exposed to outside at an intermediate portion between the front and back end portions through a separation area between the ventral- and back-side outer sheets at the crotch portion. If the liquid impervious sheet is not covered on the under surface, the liquid impervious sheet is exposed between the ventral- and back-side outer sheets. Since the liquid impervious sheet is different in appearance and texture from the ventral- and back-side outer sheets, the liquid impervious sheet is preferably covered with a nonwoven fabric not so as to be exposed, as described in Patent Document 1.

Patent Document 1: JP 2005-027839 A

DISCLOSURE OF THE INVENTION

Technical Problems to be Solved

However, the conventional two-separated disposable diaper has a problem of lower air permeability at a waist portion, as compared with an underpants type disposable diaper with a single-piece outer sheet.

Accordingly, a main object of the present invention is to improve air permeability of a diaper at a waist portion.

Means to Solve the Problem

The present invention for solving the foregoing problem is as follows:

<First Aspect of the Invention>
An underpants type disposable diaper, comprising:
a barrel-shaped waist portion that includes a ventral-side outer sheet for covering a waist of a wearer on a ventral side and a back-side outer sheet for covering a waist of a wearer on a back side, in which the ventral- and back-side outer sheets are joined together at joined sections at edges on the both sides in a width direction, and the ventral- and back-side outer sheets are not connected but separated at a crotch portion; and an absorber that is connected at a front end portion to the ventral-side outer sheet on an inner surface at a central portion in the width direction and is connected at a back end portion to the back-side outer sheet on an inner surface at a central portion in the width direction, in which an intermediate portion between the front and back end portions is exposed to outside from a separation area between the ventral- and back-side outer sheets at the crotch portion, wherein the absorber has a liquid pervious top sheet arranged on a top side, a liquid impervious sheet arranged on an underside, and an absorbent element interposed between the foregoing sheets to absorb and retain a liquid, a crotch outer sheet is laminated on an underside of the liquid impervious sheet in the absorber so as to be exposed to on an external surface of a product, and the crotch outer sheet is higher in stiffness than sheets constituting the ventral- and back-side outer sheets.

Operation and Effect

With such an arrangement as described above, it is possible to add elasticity to the outer part around a boundary between a laminated section of the back- and ventral-side outer sheets and a section at which the absorber is exposed, with an increased fit.

<Second Aspect of the Invention>

In the underpants type disposable diaper according to the second aspect of the present invention, the crotch outer sheet is disposed in an area ranging in a front-back direction from an intermediate position between the front end portion of the absorber and a crotch-side side edge of the ventral-side outer sheet to an intermediate position between the back end portion of the absorber and a crotch-side side edge of the back-side outer sheet.

<Third Aspect of the Invention>

In the underpants type disposable diaper according to the third aspect of the present invention, the underpants type disposable diaper includes: a front-side outer nonoverlap section defined by an area ranging in the front-back direction from the front end portion of the absorber to the front end portion of the crotch outer sheet; a front-side outer overlap section in which the front end portion of the crotch outer sheet and the crotch-side side end of the ventral-side outer sheet overlap each other; a back-side outer nonoverlap section defined by an area in the front-back direction ranging from the back end portion of the absorber to the back end portion of the crotch outer sheet; and a back-side outer overlap section in which the back end portion of the crotch outer sheet and the crotch-side side end of the back-side outer sheet overlap each other, and assuming that the number of sheets constituting the outer sheets on the underside of the liquid impervious sheet is B1 at the intermediate portion, A1 at the front- and back-side outer overlap sections, and C1 at the front- and back-side outer nonoverlap sections, there is established a relationship of B1<C1<A1.

(Operation and Effect)

The cause of lower air permeability was initially unknown. After repeated keen investigations, the inventor has found out that a conventional diaper was lowered in air permeability at the waist portion because the under surface of the absorber was entirely covered with a nonwoven fabric, which means that the nonwoven fabric lies unnecessarily on overlap sections of the waist portion and the absorber.

In light of the finding, the inventor has accomplished the present invention in which: no crotch outer sheet is provided on the under surface of the absorber in an area in the front-back direction, at a front-side part ranging from the front end portion to a site closer by a predetermined distance to the back end portion, and at a back-side part ranging from the back end portion to a site closer by a predetermined distance to the front end portion; and the crotch outer sheet is provided to the intermediate portion between the front- and back-side parts. With such an arrangement, it is possible to reduce a proportion of the crotch outer sheet at the overlap sections of the waist portion and the absorber, thereby improving air permeability at the waist portion.

In addition, according to the present invention, the proportion of the crotch outer sheet is reduced at the overlap sections of the waist portion and the absorber. Therefore, the diaper can be increased in strength and the like without lowering air permeability at the waist portion, by containing a deodorant in the crotch outer sheet so as to perform an odor-eliminating function or by changing a material for the crotch outer sheet as appropriate.

Further, according to the present invention, the outer part becomes thickest at the front- and back-side overlap sections. As a result, the diaper increases in elasticity at the foregoing sections. Accordingly, a force of resilient and elastic members is transferred more efficiently on both sides to thereby attach the absorber firmly to the body of a wearer with a higher fit, and thus the absorber becomes less prone to be shifted in position in a right-left direction while the diaper is worn. In addition, according to the present invention, the outer part is thinner at the front- and back-side outer nonoverlap sections than at the front- and back-side outer overlap sections, and is thicker than at the intermediate portion. Accordingly, the front- and back-side outer nonoverlap sections are less elastic than the front- and back-side outer overlap sections, and the front- and back-side outer nonoverlap sections fit into the curves of the upper part of abdomen and upper part of hip of a wearer.

<Fourth Aspect of the Invention>

In the underpants type disposable diaper according to the fourth aspect of the present invention, assuming that a basis weight of sheets constituting the outer sheets on the underside of the liquid impervious sheet is B2 at the intermediate portion, A2 at the front- and back-side outer overlap sections, and C2 at the front- and back-side outer nonoverlap sections, there is established a relationship of B2<C2<A2.

(Operation and Effect)

When the basis weight of the sheets on the underside of the liquid impervious sheet falls within the range as defined above, the invention becomes further effective.

<Fifth Aspect of the Invention>

In the underpants type disposable diaper according to the fifth aspect of the present invention,
 the ventral-side outer sheet and/or the back-side outer sheet have each a main unit section that constitutes an area identical in an up-down direction to the joined section, and an extension section that extends below the main unit section, and
 the overlap width of the front-side outer overlap section in the front-back direction and/or the overlap width of the back-side outer overlap section in the front-back direction are shorter than a length of the extension section in the front-back direction and are longer than ½ of the length of the extension section in the front-back direction, on each of the front and back sides.

(Operation and Effect)

When the ventral-side outer sheet and/or the back-side outer sheet have each the extension section, the absorber covers the hip and groin of a wearer on both sides at the extension section. Accordingly, setting the overlap width(s) within the range as defined above preferably increases elasticity at the overlap section of the extension section and the absorber, with an increased fit.

<Sixth Aspect of the Invention>

In the underpants type disposable diaper according to the sixth aspect of the present invention, the resilient and elastic members are fixed in an extended state in the absorber in the front-back direction on the underside of the absorbent element, at least in an area ranging in the front-back direction from a site in the back end portion to a site in the intermediate portion.

(Operation and Effect)

Meanwhile, a conventional two-separated disposable diaper has a problem that, as shown in FIG. 20, a back-side part is bent in the shape of a dogleg with a folding point as shown by an arrow in the diagram and is swelled outward. After repeated keen investigations on the cause of the bending phenomenon, the inventor has found out that, in a two-separated disposable diaper, stiffness is different between a section at which the back-side outer sheet is laminated and a section at which the absorber is exposed (the latter is lower in stiffness than the former), which causes a phenomenon of bending in the shape of a dogleg with a folding point at an outer boundary between the sections. The inventor has also discovered that the bending phenomenon is prone to occur when a wearer is in a sitting position.

Further advanced investigations have revealed that the bending phenomenon is likely to develop particularly in such a diaper with a crotch outer sheet as in the present invention. Specifically, such a diaper with a crotch outer sheet as in the present invention is different in elasticity between the sections with different numbers of overlapped outer sheets, and thus the bending phenomenon is prone to take place in particular at the back-side part.

In light of the foregoing findings, the sixth aspect of the invention has been accomplished in such a manner that the resilient and elastic members are fixed in an extended state in the absorber in the front-back direction on the underside of the absorbent element, at least in the area ranging in the front-back direction from a site in the back end portion to a site in the intermediate portion. By providing the resilient and elastic members in such a manner stated above, the resilient and elastic members exert a contraction force on an area straddling the outer boundary, thereby to fit the area to the body of a wearer, which makes the conventional bending phenomenon less prone to occur. In addition, since the outer part is the thinnest at the intermediate portion in the present invention, a contraction force of the resilient and elastic members can be more efficiently transferred to fit the absorber firmly to the body of a wearer with an increased fit.

<Seventh Aspect of the Invention>

In the underpants type disposable diaper according to the seventh aspect of the present invention, the resilient and elastic members are provided between the liquid impervious sheet and the crotch outer sheet.

(Operation and Effect)

With this arrangement, it is possible to preferably prevent the bending phenomenon as stated above, and keep the resilient and elastic members from being exposed, thereby resulting in improved appearance and easier manufacture.

<Eighth Aspect of the Invention>
In the underpants type disposable diaper according to the eighth aspect of the present invention, as the resilient and elastic members, elongated resilient and elastic members are provided in parallel in the front-back direction at the central and both side portions of the absorber in the width direction.
(Operation and Effect)
With such an arrangement of the resilient and elastic members as described above, the bending phenomenon can be preferably prevented in the overall the absorber in the width direction in an effective manner.

<Ninth Aspect of the Invention>
In the underpants type disposable diaper according to the ninth aspect of the present invention, as the elongated resilient and elastic members, rubber threads with a fineness of 470 to 1,000 dtex are fixed at an extension rate of 150 to 220% in the width direction at intervals of 10 to 100 mm.
(Operation and Effect)
When the elongated resilient and elastic members are provided in parallel in the front-back direction at the central and both side portions of the absorber in the width direction under the conditions as described above for fineness, extension rate, and intervals, the diaper becomes particularly excellent in preventing the bending phenomenon.

<Tenth Aspect of the Invention>
In the underpants type disposable diaper according to the tenth aspect of the present invention, the extension rate of the elongated resilient and elastic members provided at the central portion in the width direction is set higher than the extension rate of the elongated resilient and elastic members provided in the both side portions in the width direction.
(Operation and Effect)
With such an arrangement as described above, the diaper becomes preferably excellent in preventing the bending phenomenon and increased in fit particularly to the hip of a wearer.

<Eleventh Aspect of the Invention>
In the underpants type disposable diaper according to the eleventh aspect of the present invention, the resilient and elastic members extend by to 180 mm toward the back end portion of the absorber and extend by 5 to 180 mm toward the intermediate portion of the absorber, with reference to a boundary between the intermediate portion and the back end portion.
(Operation and Effect)
With such an arrangement within the ranges as described above, the diaper becomes particularly excellent in preventing the bending phenomenon.

<Twelfth Aspect of the Invention>
In the underpants type disposable diaper according to the twelfth aspect of the present invention, the crotch outer sheet is formed in the same width as the absorber.
(Operation and Effect)
With this arrangement, the crotch portion becomes simplified in appearance.

<Thirteenth Aspect of the Invention>
In the underpants type disposable diaper according to the thirteenth aspect of the present invention, the crotch outer sheet is formed wider than the absorber.
(Operation and Effect)
With this arrangement, the crotch outer sheet lies off the absorber on the both sides in the width direction. Accordingly, some resilient and elastic members may be arranged at the lying-off portions on the both sides to increase a fit to the legs of a wearer, or the overall crotch outer sheet may contain some deodorant to increase odor-eliminating performance around the leg portions.

<Fourteenth Aspect of the Invention>
In the underpants type disposable diaper according to the fourteenth aspect of the present invention, the crotch outer sheet is formed narrower than the absorber.
(Operation and Effect)
With this arrangement, it is possible to keep material costs down and improve air permeability at the crotch portion.

<Fifteenth Aspect of the Invention>
In the underpants type disposable diaper according to the fourteenth aspect of the present invention, a plurality of crotch outer sheets is arranged at the intermediate portion at predetermined intervals.
(Operation and Effect)
By arranging separate crotch outer sheets at intervals as described above, it is possible to cover the under surface of the absorber in a wider area while suppressing usage amounts of materials and improving air permeability.

<Sixteenth Aspect of the Invention>
In the underpants type disposable diaper according the sixteenth aspect of the present invention, an indicator is provided to the absorber at least at a section without the crotch outer sheet so as to indicate absorption of a liquid.
(Operation and Effect)
With this arrangement, it is possible to visually check an indication on the indicator through the section without the crotch outer sheet, not through the crotch outer sheet, thereby providing favorable visibility.

As stated above, the present invention provides advantages of improved air permeability at the waist portion and the like.

BEST MODE FOR CARRYING OUT THE INVENTION

Embodiments of the present invention will be further described in detail below with reference to the drawings.

First Embodiment

FIGS. 1 to 6 show one example of the underpants type disposable diaper according to the present invention. In FIG. 1, the term "front-back direction" refers to a direction that links the ventral side to the back side; the term "width direction" a direction orthogonal to the front-back direction; and the term "up-down direction" a direction orthogonal to a waist direction, in other words, a direction that links a waist opening WO to a crotch portion.

The underpants type disposable diaper 10 has a ventral-side outer sheet 12F that covers a ventral side of a waist of a wearer, and a back-side outer sheet 12B that covers a back side of the waist of the wearer. The ventral-side outer sheet 12F and the back-side outer sheet 12B are joined together at joined sections 12A at edges on both sides in the width direction by heat sealing, ultrasonic welding or the like, thereby forming a barrel-shaped waist portion. The ventral-side outer sheet 12F and the back-side outer sheet 12B are not connected but separated at the crotch portion. A separation distance Y may be about 150 to 250 mm.

As illustrated, if the ventral-side outer sheet 12B extends below the joined sections 12A, it is possible to provide an extension welding section that is integrally processed by heat sealing or the like in an area containing an extending portion in the up-down direction. By providing the extension welding section, it is possible to prevent that second elongated resilient and elastic members 16 are drawn in at an extension section 14 described later. In a general joint pattern, the joined sections 12A each include a series of small welding points for a lower proportion of a welded area, in consideration of easiness to tear off the diaper on the both sides. However, since there is no need to consider easiness to tear for the extension welding section, the proportion of a welding area may be made higher at the extension welding section than at the joined sections 12A, so that the second elongated resilient and elastic members 16 can be welded and fixed in a reliable manner. Alternatively, the extension welding section may be welded in a curved line at an edge of hip cover portion 14C to thereby prevent the second elongated resilient and elastic members 16 from being drawn in at the hip cover portion 14C.

In addition, the absorber 20 is connected on an under surface of a front end portion 21 to the ventral-side outer sheet 12F on an inner surface of a central portion in the width direction at the waist portion, and is connected on an under surface of a back end portion 22 to the back-side outer sheet 12B on an inner surface of a central portion in the width direction at the waist portion. An intermediate portion 23 between the front end portion 21 and the back end portion 22 is exposed to outside through the separation section Y at the crotch portion between the ventral-side outer sheet 12F and the back-side outer sheet 12B.

As seen from FIGS. 5 and 6, an upper opening at the waist portion constitutes the waist opening WO through which the waist of a wearer passes, and sections surrounded by a lower edge of the waist portion and side edges of the absorber 20 on the both sides in the width direction of the absorber 20 constitute leg openings LO through which the legs of a wearer pass. The diaper has the shape of a sand clock in the state of being torn off and opened at the joined sections 12A as shown in FIG. 1. The absorber 20 extends and covers from the back side through the crotch portion to the ventral side, and is intended to receive excreted objects, and absorb and retain body liquids. The waist portion is designed to hold the absorber 20 to a wearer.

(Waist Portion)

The ventral-side outer sheet 12F and the back-side outer sheet 12B are formed by laminating two sheets S1 and S2 of a nonwoven fabric or the like, and have elongated resilient and elastic members 15 and 16 of rubber threads or the like between the two sheets S1 and S2 at a predetermined extension ratio for an increased fit to the waist of a wearer, as shown in FIG. 4. Such a nonwoven fabric may be any of various nonwoven fabrics, such as a spun-bonded nonwoven fabric, a melt-blown nonwoven fabric, a point-bonded nonwoven fabric, an air-through nonwoven fabric, an air-point nonwoven fabric, a spun-lace nonwoven fabric, an SMS nonwoven fabric, and the like, which are made of fibers of PP, PP/PE, PP/PET, or the like.

More specifically, the back-side outer sheet 12B has a main unit section 13 that covers an area in the up-down direction identical to the joined sections 12A, and the extension section 14 that extends below the main unit section 13. The extension section 14 has a central portion 14M that overlaps the absorber 20 in the width direction and the hip cover portion 14C that extends on both sides of the central portion 14M.

The extension section 14 can be formed in an arbitrary shape, and in an illustrated example, the extension section 14 extends at an upper end below the main unit section 13, with the same width as the main unit section 13, and the extension section 14 is made narrower on a lower side with an increasing proximity to the crotch portion. The extension section 14 may be omitted at a section with the same width as the main unit section 13. With such an arrangement, an outer edge 14e in the width direction of the hip cover portion 14C forms a straight or curved line toward the absorber 20 with increasing proximity to the crotch portion, whereby the hip cover portion 14C is shaped so as to cover the hip of a wearer in an easy manner. Dimensions of the extension section 14 may be decided as appropriate, and more preferably, a length 14x of the hip cover portion 14C in the width direction (a maximum separation distance in the width direction between the outer edge 14e of the hip cover portion 14C and a side edge of the absorber 20 in the width direction) is 80 to 160 mm, and a length 14y of the hip cover portion 14C in the up-down direction (an extension length) is 30 to 80 mm. In addition, assuming that an area of a square defined by a widest section of the extension section 14 in the width direction and a widest section of the extension section 14 in the up-down direction is designated as S, the area of the extension section 14 is preferably about 20 to 80%, more preferably about 40 to 60% of S, which makes the hip portion excellent in appearance and fit.

The main unit section 13 is conceptually divided into an upper portion (waist portion) W and a lower portion U in the up-down direction. Although ranges of the portions vary depending on the size of the diaper, the upper portion W may be 15 to 80 mm long in the up-down direction, and the lower portion U may be 35 to 220 mm long in the up-down direction.

A plurality of waist resilient and elastic members 17 are fixed to the upper portion (waist portion) W of the main unit section 13 in the width direction, in an extended state at a predetermined extension ratio at intervals in the up-down direction, so as to be made entirely continuous in the width direction. In addition, out of the waist resilient and elastic members 17, one or more provided in a section adjacent to the lower portion U of the main unit section 13 may overlap the absorber 20 or may lie on the main unit section 13 on the both sides in the width direction, except for the central portion in the width direction that overlaps the absorber 20. As the waist resilient and elastic members 17, about 3 to 22 rubber threads with a fineness of about 300 to 2,000 dtex, in particular about 400 to 1,900 dtex (in the case of synthetic rubber. For natural rubber, about 0.1 to 1.5 $mm^2$, particularly 0.1 to 1.0 $mm^2$, in cross-section area) are preferably fixed at intervals of 4 to 12 mm at an extension ratio of about 200 to 400%, in particular 220 to 320%. In addition, the waist resilient and elastic members 17 do not need to be all the same in fineness and extension ratio, and may be different in fineness and extension ratio between the upper and lower sides of the waist portion, for example. The waist resilient and elastic members 17 can be freely defined regardless of magnitude with respect to the first and second elongated resilient and elastic members 15 and 16.

In addition, a plurality of first elongated resilient and elastic members 15 is fixed to the lower portion U of the main unit section 13, in an extended state in the width direction at a predetermined extension ratio at some intervals in the up-down direction, in an area above and on both sides of the absorber 20 in the width direction, except for the central portion that overlaps the absorber 20 in the width direction, so as to be made entirely continuous in the width direction. An arrangement area of the first elongated resilient and elastic members 15 in the up-down direction may be only a portion of the main unit section 13, but preferably ranges over the substantially entire main unit section (an area on which an elastic force of the members acts entirely).

As the first elongated resilient and elastic members 15, about 5 to 30 rubber threads with a fineness of about 300 to 1,200 dtex, particularly about 400 to 1,000 dtex (in the case of synthetic rubber. For natural rubber, about 0.1 to 1.0 $mm^2$, particularly about 0.1 to 0.8 $mm^2$, in cross-section area) are preferably fixed at intervals of 3 to 8 mm at an extension ratio of about 150 to 300%, preferably about 240 to 300%.

In addition, a plurality of second elongated resilient and elastic members 16 is fixed to the extension section 14, in an extended state at a predetermined extension ratio in the width direction, at some intervals in the up-down direction, in an area on the both sides of the absorber 20, except for the central portion that overlaps the absorber 20 in the width direction, so as to be made entirely continuous in the width direction (at least over the entire hip cover portion 14C). An arrangement area of the second elongated resilient and elastic members 16 may be only a portion of the extension section 14, but preferably ranges over the substantially entire extension section 14 (an area on which an elastic force of the members acts entirely).

As the second elongated resilient and elastic members 16, about 3 to 10 rubber threads with a fineness of about 300 to 1,200 dtex, particularly about 400 to 1,000 dtex (in the case of synthetic rubber. For natural rubber, about 0.1 to 1.0 mm$^2$, particularly about 0.1 to 0.8 mm$^2$, in cross-section area) are preferably fixed at intervals of 3 to 8 mm at a higher extension ratio than that in the first elongated resilient and elastic members, within a range of 240 to 400%, particularly a range of 280 to 360%. The second elongated resilient and elastic members 16 have a higher extension ratio at the both ends in the up-down direction than at the intermediate portion. The second elongated resilient and elastic members 16 have preferably the same fineness as the first elongated resilient and elastic members 15, or may have larger or smaller fineness than the first elongated resilient and elastic members 15. The waist resilient and elastic members 17 and the elongated resilient and elastic members 15 and 16 may use synthetic rubber or natural rubber.

As stated above, when the second elongated resilient and elastic members 16 are higher in extension ratio than the first elongated resilient and elastic members 15, an obliquely upward force linking the crotch portion and the both joined sections 12A is exerted on the hip cover portion 14C at a deeper angle θ and at a high degree of strength, as shown by a hollow arrow in FIG. 6. Accordingly, the hip cover portion 14C becomes less prone to ride up or bulge, resulting in a favorable fit to the body of a wearer. When configuring the ventral-side outer sheet 12F and/or the back-side outer sheet 12B, the nonwoven fabrics S1 and S2 can be adjusted in extension in the width direction such that a larger tensile force is applied to S2 than S1, whereby the hip cover portion 14C can be curled inward with a further increased fit to the hip of a wearer.

Meanwhile, the ventral-side outer sheet 12F is basically the same as the main unit section 13 in the back-side outer sheet 12B, and has the shape of a rectangle extending around the waist portion, and does not have the extension section 14 unlike the back-side outer sheet 12B. Therefore, the same constitutional elements of the ventral-side outer sheet 12F as those of the back-side outer sheet 12B are given the same reference numerals as those of the back-side outer sheet 12B, and description thereof will be omitted. The ventral-side outer sheet 12F may also be configured as to include the main unit section and the extension section, as with the back-side outer sheet 12B.

Meanwhile, as shown in the diagram, in an arrangement with the first and second elongated resilient and elastic members 15 and 16 on the both sides in the width direction except for the central portion that overlaps the absorber 20 in the width direction, the resilient and elastic members may exist only on the both sides in the width direction. Alternatively, in such an arrangement, the resilient and elastic members may straddle the absorber 20 in the width direction from one to the other sides of the absorber 20, and be cut off at the central portion that overlaps the absorber 20 in the width direction so as to exert no elastic force (this is virtually equal to no provision of the resilient and elastic members). Further, in the present invention, the first and second elongated resilient and elastic members 15 and 16 may also straddle the absorber 20 in the width direction from one to the other sides of the absorber 20 so that an elastic force can act entirely on the main unit section 13 and the extension section 14 in the width direction.

The second elongated resilient and elastic members 16 are not welded at the joined sections 12A on the side edges to the sheets S1 and S2, unlike the first elongated resilient and elastic members 15. Accordingly, in particular when making the second elongated resilient and elastic members 16 higher in extension ratio than the first elongated resilient and elastic members 15, the second elongated resilient and elastic members 16 are preferably subjected to some process for prevention of a drawn-in phenomenon. For this end, an adhesive can be applied directly to the second elongated resilient and elastic members 16 for an increased adhesive strength, for example. However, using a large amount of adhesive may deteriorate the resilient and elastic part in texture, and hence one preferred means is to provide an extension welding section extending from the joined sections 12A as described above.

Moreover, in an arrangement in which the second elongated resilient and elastic members 16 are cut off at the central portion in the width direction overlapping the absorber 20 for elimination of an elastic force, as described above, the second elongated resilient and elastic members 16 are preferably subjected at the ends of the central portion in the width direction to a similar process for prevention of a drawn-in phenomenon. When welding and fixing the second elongated resilient and elastic members 16 at the ends to the sheets S1 and S2, for example, the second elongated resilient and elastic members 16 may be welded in approximately straight welding lines arranged so as to traverse longitudinally the second elongated resilient and elastic members 16 arranged in the width direction.

Alternatively, the second elongated resilient and elastic members 16 may be welded to the sheets S1 and S2 with an increased adhesive strength by using a method for welding and fixing sheets described below singly or in combination with the above-described method.

(Absorber)

The absorber 20 may take any shape, and is of a rectangle in the illustrated arrangement. As shown in FIG. 3, the absorber 20 includes a top sheet 30 formed of a nonwoven fabric, for example, that lets a liquid pass through, and an absorbent element 50, in this order from a usage side. In general, a liquid impervious sheet 70 formed of a plastic sheet or the like is provided on the underside of the absorbent element 50. A crotch outer sheet 12M is provided on the underside of the liquid impervious sheet 70. In addition, to transfer a liquid having passed through the top sheet 30 quickly to the absorbent element 50, an intermediate sheet (second sheet) 40 may be interposed between the top sheet 30 and the absorbent element 50. Further, to prevent leakage of an excreted object to the both sides of the absorber 20, barrier cuffs 60 and 60 may be erected on the both sides of the absorber 20. Although not shown, constituent members of the absorber 20 can be fixed to each other by solid, bead or spiral application of a hot-melt adhesive or the like.

The absorber 20 may be detachably connected to the ventral-side outer sheet 12F and/or the back-side outer sheet 12B using mechanical fasteners or adhesive materials.

(Top Sheet)

The top sheet 30 has a liquid pervious property. Therefore, a material for the top sheet 30 only needs to have liquid perviousness, and may be a porous or nonporous nonwoven fabric or a porous plastic sheet, for example. In addition, there is no particular limitation on raw fibers for use in such a nonwoven fabric. For example, the raw fibers may be any of synthetic fibers based on olefin such as polyethylene or polypropylene, polyester, polyamide or the like, recycled fibers such as rayon or cupra, natural fibers such as cotton, mixed or composite fibers of two or more of the foregoing fibers. Further, the nonwoven fabric may be produced by any processing method. For example, such a processing method may be any known method such as a spun lace method, spun bonding method, thermal bonding method, melt-blown method, needle punching method, air-through method, and point bonding method. For example, if flexibility and drape property are needed, the spun lace method or the spun lace method is preferred. If high bulk and softness are required, the air-through method, the point bonding method, or the thermal bonding method is preferred.

In addition, the top sheet 30 may be a single sheet or a laminated sheet obtained by sticking two or more sheets to each other. Similarly, the top sheet 30 may be a single sheet or two or more sheets in a planar direction.

(Interlayer Sheet)

To rapidly move a fluid having permeated through the top sheet 30 to the absorbent body, the interlayer sheet (also called "second sheet") 40 may be provided, which is higher in fluid permeability rate than the top sheet 30. The interlayer sheet 40 allows a fluid to move quickly to the absorbent body to thereby enhance an absorption performance of the absorbent body, and prevents a "backflow" phenomenon in which a fluid flows back from the absorbent body to thereby keep the top sheet 30 in a dry condition. The interlayer sheet 40 may be omitted.

The interlayer sheet 40 may use the same material as that of the top sheet 30, or may use a spun lace, a pulp nonwoven fabric, a mixed sheet of pulp and rayon, point-bonded or crepe paper, for example. In particular, an air-through nonwoven fabric or a spun-bonded nonwoven fabric is preferred.

Although, in the illustrated embodiment, the interlayer sheet 40 is made shorter in width than the absorbent body 56 and is centered with respect to the absorbent body 56, the interlayer sheet 40 may also be provided across a full width of the absorbent body 56. A length of the interlayer sheet 40 in the longitudinal direction may be the same as that of the absorbent body 56, or may be in a shorter range centered in an area for receiving a fluid. A typical material for the interlayer sheet 40 is a highly liquid pervious nonwoven fabric.

(Liquid Impervious Sheet)

The liquid impervious sheet 70 simply refers to a sheet provided on an underside of the absorbent body 56, and the absorbent body 56 is interposed between the liquid impervious sheet 70 and the top sheet 30 in this embodiment. There is thus no particular limitation on a material for the liquid impervious sheet 70. Specifically, the material may be any of olefin resins such as polyethylene and polypropylene, laminated nonwoven fabrics in which a nonwoven fabric is laminated on a polyethylene sheet or the like, and nonwoven fabrics to which a water-proof film is interposed for virtual liquid imperviousness (in this case, the water-proof film and the nonwoven fabric constitute a liquid impervious sheet), for example. Certainly, in addition to the foregoing examples, there are liquid impervious, moisture pervious sheets that have been favorably used in recent years from the viewpoint of prevention of stuffiness. Such a sheet made of a liquid impervious and moisture pervious material may be a microporous sheet obtained by melting and kneading an inorganic filling agent into an olefin resin such as polyethylene or polypropylene, to thereby form a sheet and then extending the sheet in a uniaxial or biaxial direction, for example. Further, the liquid impervious sheet 70 may use a sheet that is given liquid imperviousness without the use of a waterproof film, by using a nonwoven fabric of micro denier fibers, applying heat or pressure to make gaps in fibers smaller with enhanced leakage resistance, coating with high water-absorption resin or hydrophobic resin, or applying a water repellent agent.

The liquid impervious sheet 70 can be extended to the usage surface so as to wrap around the sides (not shown) to thereby prevent lateral leakage of a body fluid. In this embodiment, however, lateral leakage is prevented by interposing a second liquid impervious sheet 72 in the double barrier sheet 64 forming barrier cuffs 60. According to this embodiment, since the liquid impervious sheet 72 extends to erected portions of the barrier cuffs 60, it is possible to advantageously prevent that lateral diffusion of a body fluid along the top sheet 30 and lateral leakage of loose stool between the barrier cuffs 60 and 60.

The liquid impervious sheet may also have designed patterns prepared by printing or coloring on the inner or outer surface. In addition, the liquid impervious sheet may have a printed or colored design sheet attached to the outer surface, as a member different from the crotch outer sheet. Further, the liquid impervious sheet may include an indicator on the inner side to indicate voiding of urine by some visual change.

(Barrier Cuffs)

The barrier cuffs 60, 60 on the both sides of the absorbent article are designed to block and prevent urine or loose stool from moving and leaking laterally over the top sheet 30. The barrier cuffs 60, 60 are additional elements.

The illustrated barrier cuffs 60 are formed by laminating two water repellent nonwoven fabric barrier sheets 64 so as to cover from the underside of the absorbent element 50 to a downward folded portion of the top sheet 30, and project toward the upper side of the absorbent body 56. To block urine moving laterally over the top sheet 30, the second liquid impervious sheet 72 is interposed between the two nonwoven fabric barrier sheets 64 forming the barrier cuffs 60. Although not shown, the liquid impervious sheet 70 may be inserted at side portions into the two-layered barrier sheet 64, and extended to midpoints in the barrier cuffs 60 projecting toward the upper side.

The barrier cuffs 60 can be designed in shape as appropriate. In the illustrated example, the resilient and elastic members, e.g., rubber threads 62 are fixed in an extended state at the leading ends and middle portions of projections of the barrier cuffs 60 so that the barrier cuffs 60 are erected by a stretching force of the rubber threads 62 when the diaper is being used. In this mode, the rubber threads 62 at the middle portions are located closer to a center of the top sheet 30 as compared with the rubber threads 62, 62 at the leading ends, and are fixed at front and back end portions of the top sheet 30, and therefore the barrier cuffs 60 are erected at base portions in such a manner as to be slant to the center, and are erected at the middle portions to the leading ends in such a manner as to be slant outward, as shown in FIG. 3.

(Absorbent Element)

The absorbent element 50 has an absorbent body 56, and an envelope sheet 58 that envelops at least an under surface and side surfaces of the absorbent body 56. The envelope sheet 58 may be omitted. Further, in the illustrated embodiment, a holding sheet 80 is disposed between the absorbent body 56 and the envelope sheet 58 on the underside (lower side). The holding sheet 80 may be omitted.

(Absorbent Body)

The absorbent body 56 may be an accumulation of short fibers of fluff pulp or the like, an assembly of filaments 52, 52 . . . , or others.

The assembly of filaments 52, 52 . . . can be obtained by opening a tow (fiber bundle). Constitutional fibers for the tow may be any of polysaccharides or derivatives thereof (such as cellulose, cellulose ester, chitin, and chitosan), synthetic polymers (such as polyethylene, polypropylene, polyamide, polyester, polylactamide, and polyvinyl acetate) and the like, for example. In particular, cellulose ester or cellulose is preferred.

Usable celluloses include celluloses derived from plants such as cotton, linters and wood pulp, bacterial celluloses, and regenerated celluloses such as rayon. Regenerated celluloses may be in the form of spun fibers.

Preferably used cellulose esters include: organic acid esters such as cellulose acetate, cellulose butyrate, and cellulose propionate; mixed acid esters such as cellulose acetate propionate, cellulose acetate butyrate, cellulose acetate phthalate, and cellulose nitrate acetate; and cellulose ester derivatives such as polycaprolactone grafted cellulose ester, for example. These cellulose esters may be used singly or in combination. A viscosity average degree of polymerization of a cellulose ester is about 50 to 900 for example, preferably about 200 to 800. An average degree of substitution of a cellulose ester is about 1.5 to 3.0 (e.g. 2 to 3), for example.

An average degree of polymerization of a cellulose ester may be about 10 to 1,000 for example, preferably about 50 to 900, and more preferably about 200 to 800. An average degree of substitution of a cellulose ester may be about 1 to 3 for example, preferably about 1 to 2.15, and more preferably about 1.1 to 2.0. An average degree of substitution of a cellulose ester may be selected from a viewpoint of enhancing biodegradability.

Cellulose ester may be an organic acid ester (ester of organic acid with a carbon number of about 2 to 4, for example), and is preferably in particular a cellulose acetate. An acetylation degree of a cellulose acetate is about 43 to 62% in many cases, and preferably in particular about 30 to 50% with higher biodegradability. A particularly preferred cellulose ester is cellulose diacetate.

The tow constitutional fibers may contain various additives, for example, a heat stabilization agent, coloring agent, oil solution, retention aid, whiteness improving agent, and the like.

A fineness of the tow constitutional fibers is 1 to 16 deniers for example, preferably 1 to 10 deniers, and more preferably 1 to 6 deniers. The tow constitutional fibers may be non-crimped fibers but preferably crimped fibers. A degree of crimping of the crimped fibers may be about 5 to 75 crimps per inch, preferably about 10 to 50 crimps per inch, and more preferably about 15 to 50 crimps per inch. In many cases, uniformly crimped fibers are used. By using such crimped fibers, it is possible to produce a high-integration tow due to fiber entanglement, and manufacture a high-bulk, light-weight absorbent body. There is no particular limitation on a cross-section shape of the tow constitutional fibers, and the tow constitutional fibers may be circular, elliptic, odd (e.g. Y, X, I, or R letter) or hollow in cross section, for example. The tow constitutional fibers can be used as a tow (fiber bundle) of about 1,000 to 1,000,000 single fibers for example, preferably about 2,000 to 1,000,000 single fibers. Such a fiber bundle is preferably formed by binding about 1,000 to 1,000,000 continuous fibers.

Bales of tow of cellulose diacetate preferably used in the present invention are made commercially available by Celanese Corp., Daicel Chemical Industries, Ltd., and others. A bale of tow of cellulose diacetate is about 0.5 g/cm$^3$ in density and 400 to 600 kg in gross weight. The tow is peeled off from the bale and opened in a wide belt-like form of desired size and bulk. An opening width of the tow can be arbitrarily decided, for example 50 to 2,000 mm, preferably about 50 to 300 mm, so as to be adapted to the width of the absorbent body in the diaper. In addition, the density of the absorbent body can be adjusted by controlling a degree of tow opening.

Preferably, high-absorbent polymer particles 54, 54 . . . are contained in the absorbent body 56, as shown in FIG. 3. In addition, at least in an area receiving a fluid, high-absorbent polymer particles (SAP particles) are desirably scattered in a virtually overall thickness direction with respect to the assembly of filaments 52, 52 . . . . FIG. 3 is a conceptual enlarged view of the particles scattered in the virtually overall thickness direction.

If there are no or few if any, SAP particles in upper, lower and middle portions of the absorbent body 56, it is not recognized that "the SAP particles are scattered in the overall thickness direction". Therefore, the "scattered in the overall thickness direction" state refers to a mode in which the particles are scattered "evenly" in the overall thickness direction with respect to the assembly of filaments, or a mode in which the particles are "unevenly distributed" in the upper, lower and/or middle portions but still are scattered in the upper, lower and/or middle portions. In addition, the foregoing state does not exclude a mode in which some of the SAP particles does not enter into the assembly of filaments 52, 52 . . . and remain on a surface of the same, or a mode in which some of the SAP particles pass through the assembly of filaments 52, 52 . . . and exist on the envelope sheet 58 or the holding sheet 80.

(High-Absorbent Polymer Particles)

The high-absorbent polymer particles 54 may be not only "particles" but also "powders". A particle diameter of the high-absorbent polymer particles 54 may be the same as that of particles used in this kind of absorbent articles, and is 1,000 μm or less, desirably in particular 150 to 400 μm. There are no particular limits on a material for the high-absorbent polymer particles 54, and a preferred material is 40 g/g or more in capacity of water absorption. The high-absorbent polymer particles 54 may be based on starch, cellulose or synthetic polymer, and may use starch-acrylic acid (salt) graft copolymer, saponified product of starch-acrylonitrile copolymer, cross-linked sodium carboxymethyl cellulose, acrylic acid (salt) polymer, or the like. A shape of the high-absorbent polymer particles 54 is preferably a commonly used particulate shape, and may also be any other shape.

The high-absorbent polymer particles 54 preferably deliver a water absorption speed of 40 seconds or less. If the water absorption speed exceeds 40 seconds, a backflow phenomenon becomes prone to occur, where a fluid supplied to the absorbent body 56 flows back out of the absorbent body 56.

In addition, the high-absorbent polymer particles 54 are preferably 1,000 Pa or more in gel strength. This prevents effectively a sticky feel after absorption of a fluid even if the absorbent body 56 is high in bulk.

A basis weight of the high-absorbent polymer particles 54 may be decided as appropriate in accordance with an absorption capacity required for the absorbent body 56, and may be 50 to 350 g/m$^2$, although it is not always defined so. By setting the basis weight of the polymers at 50 g/m$^2$ or less, it is possible to prevent that weight reduction becomes less effective due to the weight of the polymers when synthetic continuous fibers are used. If the basis weight exceeds 350 g/m², the high-absorbent polymer particles 54 become saturated in effectiveness and an excessive amount thereof has an unpleasant grainy feel.

If necessary, the high-absorbent polymer particles 54 can be adjusted in density or amount of dispersion in the planar direction of the absorbent body 56. For example, an amount of dispersion may be made larger at a fluid excreted portion than other portions. With regard to a difference between the sexes, the dispersion density (amount) may be increased at the front side portion for men or increased at the middle portion for women. The absorbent body 56 may have a local portion (in spot, for example) with no polymer in the planer direction thereof.

As needed, a plurality of high-absorbent polymer particles 54 with different particle size distributions can be provided in sequence in the thickness direction, such that the particles with smaller particle size distributions are located on the lower portion of the absorbent body 56, and the particles with larger particle size distributions on the upper portion of the same.

Proportions of the high-absorbent polymer particles 54 and the continuous fibers affect an absorbing property. A weight ratio of the high-absorbent polymer particles to the continuous fibers in a planar area of 5×5 cm directly receiving a fluid in the absorbent body 56, is 1 to 14, desirably 2 to 9 in particular.

(Envelope Sheet)

The envelope sheet 58 may use any of materials such as tissue paper, particularly crepe paper, nonwoven fabrics, polyethylene-laminated nonwoven fabrics, foraminous sheets, and the like. The sheet desirably does not let high-absorbent polymer particles pass through. In using a nonwoven fabric instead of crepe paper for the envelope sheet 58, a hydrophilic SMMS (spun bonded/melt-blown/melt-blown/spun-bonded) nonwoven fabric is preferred in particular. A material for such a fabric may be polypropylene, polyethylene/polypropylene, or the like. A basis weight of the fabric is 5 to 40 g/m², desirably 10 to 30 g/m² in particular.

The envelope sheet 58 may be configured as to envelop an overall layer containing the assembly of continuous fibers 52, 52 . . . and the high-absorbent polymer particles 54, 54 . . . as shown in FIG. 3, or may envelop only under and side surfaces of the layer. Further, although not shown, the envelope sheet 58 may be configured as to cover the upper and side surfaces of the absorbent body 56 with crepe paper or a nonwoven fabric, and cover the under surface of the same with a liquid impervious sheet of polyethylene or the like, or as to cover the upper surface of the absorbent body 56 with crape paper or nonwoven fabric and cover the side and under surfaces of the same with a liquid impervious sheet of polyethylene or the like (the foregoing materials are constitutional elements of the envelope sheet). If necessary, the envelope sheet 58 may be configured in such a manner that the layer containing the assembly of continuous fibers 52, 52 . . . and the high-absorbent polymer particles 54, 54 . . . is sandwiched between two upper and lower sheets, or in such a manner that one sheet is disposed only on the lower surface of the layer. However, these configurations are not desired because they make it difficult to prevent movement of the high-absorbent polymer particles.

(Holding Sheet)

In providing the holding sheet 80, the high-absorbent polymer particles 54 may be interposed by dispersing or the like between the holding sheet 80 and the absorbent body 56. The high-absorbent polymer particles 54 may pass through the assembly of the continuous fibers 52 during a process of supply to the assembly of the continuous fibers 52, a process subsequent to the foregoing process, or a process of distribution to consumers. The high-absorbent polymer particles having passed through the assembly of continuous fibers may bring an unpleasant grainy feel with asperities thereof to a user who touches the product by hand. To solve this problem, it is preferred to interpose the holding sheet 80 capable of holding the high-absorbent polymers 54 between the absorbent body 56 and the envelope sheet 58. The holding sheet 80 increases elasticity which would not be sufficiently provided by the envelope sheet 58 alone made of tissue paper (crepe paper) or the like, and reduces or prevents an unpleasant feel given to a user who touches the product by hand.

There is no particular limitation on a material for the holding sheet 80, and such a material only needs to be capable of holding the high-absorbent polymers 54. Specifically, the material may be any of nonwoven fabrics, crimped pulp, low-absorbent cotton fibers (e.g. fat cotton fibers, defatted cotton fibers, rayon fibers processed with a water repellent agent or a hydrophobizing agent), polyethylene fibers, polyester fibers, acrylic fibers, polypropylene fibers, silk, cotton, hemp, nylon, polyurethane, acetate fibers, and the like, for example.

If the holding sheet 80 is formed by a nonwoven fabric, the holding sheet 80 is 0.01 to 10.00 gfcm/cm², preferably 0.01 to 1.00 gfcm/cm² in compression energy, and is 10 to 100%, preferably 70 to 100% in compression resilience, on the basis of test results from KES Test.

A purpose of providing the holding sheet 80 is, as stated above, to hold the high-absorbent polymers 54 which have dropped (slipped) downward from the absorbent body 56, for example. Therefore, the dropped high-absorbent polymers 54 come into contact with a user via the envelope sheet 58 and the holding sheet 80, and thus there is no fear of giving the user an unpleasant grainy feel. In particular, the nonwoven fabric within the above-mentioned ranges of compression energy and compression resilience can perform sufficiently function thereof.

In addition, since the slipped high-absorbent polymers 54 are held by the holding sheet 80 and thus do not move over the envelope sheet 58, there is no fear of uneven absorption capabilities. Particularly, to prevent movement of the high-absorbent polymer particles 54 over the holding sheet 80, the holding sheet 80 may be coated in advance with a sticky hot-melt adhesive or the like. Alternatively, to prevent movement of the high-absorbent polymer particles 54 over the holding sheet 80, the upper surface of the holding sheet 80 (facing to the usage surface-side) may be made rough. For this purpose, the nonwoven fabric may be manufactured in such a manner that a surface thereof is roughed or fluffed by making non-netted, marbling, needle-punching, or brushing.

The holding sheet 80 may be provided only underneath the absorbent body 56 as shown in FIG. 3, or may pass by the absorbent body 56, roll and extend to the upper surface of the absorbent body 56, although not shown. In addition, a stack of a plurality of holding sheets 80 may be used.

Although, in the above example, the holding sheet 58 is disposed between the absorbent body 56 and the envelope sheet 58 on the lower side, the holding sheet may be placed underside of the envelope sheet instead (this arrangement is not shown). The important point is that providing the holding sheet 80 underside of the absorbent body 56 reduces or eliminates an unpleasant grainy feel which would be given to a user who touches the product from the under surface thereof.

(Crotch Outer Sheet)

The crotch outer sheet 12M is provided underside of the absorber 20 and exposed on the external surface of the product. A material for the crotch outer sheet 12M may be the same as those of the ventral-side outer sheet 12F and the back-side outer sheet 12B, or may be different with higher strength or a deodorant from those of the ventral-side outer sheet 12F and the back-side outer sheet 12B. More specifically, the material may be any of various nonwoven fabrics such as a spun-bonded nonwoven fabric, a melt-blown nonwoven fabric, a point-bonded nonwoven fabric, an air-through nonwoven fabric, an air-point nonwoven fabric, a spun-lace nonwoven fabric, and an SMS nonwoven fabric, which are formed by fibers of PP, PP/PE, or PP/PET, or any of the foregoing nonwoven fabrics to which a deodorant or the like is added.

In a particularly preferred material combination, the ventral-side outer sheet 12F and the back-side outer sheet 12B each have the outside sheet S1 made of a laminated nonwoven fabric such as SMS nonwoven fabric with S and M layers and the inside sheet S2 made of a PP/PE spun-bonded nonwoven fabric, and the crotch outer sheet 12M is made of a PP/PE spun-bonded nonwoven fabric.

When a wearer is in a sitting position, a high body pressure is applied to the crotch outer sheet 12M. Accordingly, the crotch outer sheet 12M is preferably made of a material with high fastness to rubbing (causing no fluff), in particular, a material which has received a rating of "□" or "○" in testing for fastness to rubbing described below.

(Fastness-to-Abrasion Testing)

Fastness to rubbing is pursuant to JIS L 0849 and is measured by a method explained below: a 250×25-mm sheet piece for measurement of fastness to abrasion is prepared and measured in fastness to rubbing on an outer surface (outer surface of an absorber). Fastness to rubbing can be measured by a color fastness rubbing tester (produced by Tester Sangyo Co., Ltd., model: AB-301). In measurement, the friction tester II type is used to vibrate the sheet piece 50 times. After the test, the resultant sheet piece is visually compared with a limit sample, and is rated on four scales (□: non-occurrence of twisted balls or fluff, ○: non-occurrence of twisted balls and occurrence of fluff, Δ: occurrence of twisted balls and fluff, and ×: breakage of nonwoven fabric).

The crotch outer sheet 12M may include some design elements prepared by printing or coloring. In combination with the above-mentioned design sheet, the crotch outer sheet 12M and the design sheet are preferably arranged such that the design matters on the two sheets do not overlap.

The crotch outer sheet 12M uses preferably a resilient and elastic nonwoven fabric which is extended and attached in a longitudinal direction of the absorber 20, thereby increasing a fit at the crotch portion.

If the absorbent body 56 is an ultra-thin absorber which is 100 g/m$^2$ or less in fiber mass per unit area and 100 g/m$^2$ or more in high-absorbent polymer mass per unit area, the absorbent body 56 has no significant elasticity and needs to be made more elastic at the crotch portion while avoiding deterioration in easiness to wear. Meanwhile, the absorbent body 56 does not need to be so elastic at the ventral- and back-sides. Therefore, if the absorbent body 56 is a general absorber or particularly a non-elastic absorber, the crotch outer sheet 12M preferably uses a sheet with high stiffness (elasticity). Such an arrangement can also prevent the conventional bending phenomenon. More specifically, the crotch outer sheet 12M uses preferably a sheet in which a sum of stiffness in machine direction and cross direction measured by the Clark test (JIS L1096 test) is 100 mm or more, preferably 150 mm or more, and the sheets S1 and S2 constituting the ventral- and back-side outer sheets 12F and 12B preferably use each a sheet in which a sum of stiffness in machine direction and cross direction is 100 mm or less, in particular 80 mm or less.

In the illustrated example, the crotch outer sheet 12M is sandwiched between the absorber 20 and the ventral- and back-side outer sheets 12F, 12B at sections in which the ventral- and back-side outer sheets 12F, 12B and the absorber 20 overlap each other. Alternatively, the crotch outer sheet 12M may be attached to outside the ventral- and back-side outer sheets 12F, 12B. The latter is preferred in an arrangement as shown in FIG. 7 described later, and is further particularly preferred in an arrangement with the resilient members on the both sides of the crotch outer sheet 12M. The crotch outer sheet 12M is attached to the under surface of the absorber 20 and the inner surfaces or outer surfaces of the ventral- and back-side outer sheets 12F and 12B by a hot-melt adhesive, or the like.

Characteristically, the absorber 20 has on the underside in an area in the front-back direction, an outer nonoverlap section 20F ranging from the front end portion to a predetermined position closer to the front end portion from the crotch-side edge of the ventral-side outer sheet 12F, an outer overlap section X ranging from the crotch-side edge of the outer nonoverlap section 20F to the crotch-side edge of the ventral-side outer sheet 12F, an intermediate portion 23, an outer nonoverlap section 20B ranging from the back end portion to a predetermined position closer to the back end portion from the crotch-side edge of the ventral-side outer sheet 12F, and an outer overlap section Z ranging from the crotch-side edge of the outer nonoverlap section 20B to the crotch-side edge of the back-side outer sheet 12B. The crotch outer sheet 12M is provided only in an area 20M ranging from the front-side outer overlap section X through the intermediate portion 23 to the back-side outer overlap section Z. In the illustrated example, the crotch outer sheet 12M covers the overall area 20M ranging from the front-side outer overlap section X through the intermediate portion 23 to the back-side outer overlap section Z. Alternatively, the outer sheet 12M may cover only part of the area 20M, as understood from the arrangement shown in FIG. 10 described later.

In addition, assuming that the number of sheets provided on the underside of the liquid impervious sheet 70 (in this embodiment, the sheets S1, S2 constituting the outer sheets 12F, 12B, and the sheet constituting the crotch outer sheet 12M) is B1 at the intermediate portion 23, A1 at the front-side outer overlap section X and the back-side outer overlap section Z, and C1 at the front side nonoverlap section 20F and the back-side outer nonoverlap section 20B, there is established in particular a relationship of B1<C1<A1. Although there are no limitations on the numbers of sheets at the foregoing portions so far as the foregoing relationship is satisfied, B1 is preferably zero or more, more preferably one in particular, and a difference between A1 and B1 is preferably two or more, and A1 is preferably five at maximum. In one particular preferred combination, B1 is one, C1 is two, and A1 is three. The front and back sides may be the same or different in number of overlapped sheets. In counting the numbers of sheets at the portions, members not affecting air permeability or stiffness are excluded, such as a small-sized disposal tape, for example.

Such an arrangement as described above reduces a proportion of the crotch outer sheet 12M to the overlap section between the waist portion and the absorber 20, thereby improving air permeability at the waist portion. In addition, the crotch outer sheet 12M may contain a deodorant to perform an odor-eliminating function, or a material for the crotch outer sheet 12M may be changed as appropriate, without lowering air permeability at the waist portion, whereby the diaper can be enhanced in strength and the other.

The length of each part in the diaper in the front-back direction can be decided as appropriate. In particular, the length of the outer overlap section X in the front-back direction where the front end portion of the crotch outer sheet 12M and the crotch-side end of the ventral-side outer sheet 12F overlap each other, and the length of the outer overlap section Z in the front-back direction where the back end portion of the crotch outer sheet 12M and the crotch-side end of the back-side outer sheet 12B overlap each other, may each be, for example 0 to 100 mm, preferably 10 to 80 mm, in particular preferably 20 to 60 mm. In addition, if the ventral-side outer sheet 12F and/or the back-side outer sheet 12B include the main unit section and the extension section, the length(s) of the outer overlap section X and/or the outer overlap section Z in the front-back direction are preferably shorter than the length of the extension section on the ventral and back sides (front and back sides), and longer than ½ of the length of the extension section in the front-back direction. If these overlap widths become excessively large, it is difficult to prevent decrease in air permeability at the waist portion. If these overlap widths become excessively small, it is not possible to obtain a desired degree of elasticity. However, the front end portion of the crotch outer sheet 12M and the lower end of the ventral-side outer sheet 12F may be separated, and the back end portion of the crotch outer sheet 12M and the lower end of the back-side outer sheet 12B may be separated.

In addition, assuming that a basis weight of the sheets provided on the underside of the liquid impervious sheet is B2 at the intermediate portion 23, A2 at the front-side outer overlap section X and the back-side outer overlap section Z, and C2 at the front-side outer nonoverlap section 20F and the back-side outer nonoverlap section 20B, there is preferably established a relationship of B2<C2<A2 in particular. Although there are no limitations on the basis weights at the foregoing sections and portions so far as the foregoing relationship is satisfied, it is preferred that B2 be 0 to 25 g/m², C2 be 10 to 50 g/m², and A2 be 15 to 75 g/m².

Meanwhile, in the examples shown in FIGS. 1 to 6, the crotch outer sheet 12M is formed of the same width as the absorber 20, in other words, the edges of the crotch outer sheet 12M on the both sides (both ends in the width direction) are aligned with the edges of the absorber 20 on the both sides (both ends in the width direction). With such an arrangement, the predetermined area 20M on the underside of the absorber 20 in the front-back direction is entirely covered with the crotch outer sheet 12M in the width direction, and the crotch outer sheet 12M does not lie off the absorber 20, which makes the crotch portion simplified in appearance.

However, the width of the crotch outer sheet 12M is not limited to the foregoing in the present invention. As shown in FIG. 7, for example, the crotch outer sheet 12M may be entirely (or partially) made wider than the absorber 20 in the front-back direction. The crotch outer sheet 12M can be arbitrarily made wider with respect to the absorber 20, and may be widened by about 10 to 60 mm (5 to 30 mm on one side), for example. With such an arrangement, the crotch outer sheet 12M lies off the absorber 20 on the both sides in the width direction. Accordingly, the crotch outer sheet 12M may have resilient and elastic members arranged on the both sides of the lying-off portions to increase a fit to the legs of a wearer, or the crotch outer sheet 12M may contain a deodorant to improve odor-eliminating performance at the leg portions.

On the other hand, the crotch outer sheet 12M may be entirely (or partially) provided narrower in the front-back direction than the absorber 20, as shown in FIGS. 8 and 9. The crotch outer sheet 12M can be arbitrarily made narrower with respect to the absorber 20, and may be narrowed by about 10 to 60 mm, for example. This makes it possible to keep material costs down and improve air permeability at the crotch portion.

When making the crotch outer sheet 12M narrower than the absorber 20, the absorber 20 may be exposed on the under surface to outside the crotch outer sheet 12M on the both sides in the width direction, depending on the sheet structure. In this embodiment, however, the barrier sheet 64 constituting the barrier cuffs 60 is brought and attached by a hot-melt adhesive or the like to the under surface of the absorber 20 on the both sides in the width direction, and the crotch outer sheet 12M overlaps on the both ends in the width direction with the ends of the barrier sheet 64 extending under the absorber 20 on the both sides in the width direction, with a predetermined overlap width W in the width direction. Accordingly, the absorber 20 is not exposed on the under surface to outside the crotch outer sheet 12M on the both sides in the width direction.

Meanwhile, the crotch outer sheet 12M may be configured as to cover singly the overall covering area, and alternatively, a plurality of crotch outer sheets 12M may be arranged so as to be adjacent to each other or spaced from each other, at least in one of the front-back direction and the width direction, as shown in FIG. 10. The crotch outer sheets 12M may be adjacent to each other, or may be arranged at a predetermined interval d to thereby cover the absorber 20 in a wider area on the under surface, while suppressing a material usage amount and improving air permeability. The interval d can be arbitrarily decided, and in general, may be about 5 to 30 mm.

Further, when arranging the crotch outer sheets 12M at the predetermined interval d, an indicator i may be provided to indicate absorption of a fluid in an area ranging in a thickness direction from the absorbent body 56-side surface of the liquid impervious sheet 70 to the liquid impervious sheet 70-side surface of the absorbent body 56, in such a manner that the indicator i overlaps the interval d. Accordingly, the indicator i can be checked with high visibility through the section without the crotch outer sheet 12M, not through the crotch outer sheet 12M. As a matter of course, the indicator may be provided at another section in the absorber 20M without the crotch outer sheet 12M.

The indicator i can be formed by applying a coating material changing in color on exposure to a fluid to the absorbent body 56-side surface of the liquid impervious sheet 70, applying such a coating material to the liquid impervious sheet 70-side surface of the absorbent body 56, or interposing a member with a coating material changing in color on exposure to a fluid between the liquid impervious sheet 70 and the absorbent body 56.

Although, in an arrangement shown in FIG. 10, a plurality of crotch outer sheets 12M are arranged in the front-back direction, the crotch outer sheets 12M may be arranged in the width direction. Preferably in particular, the crotch outer sheets 12M are arranged on the both sides at a predetermined interval in the center portion in the width direction (not shown).

(Hip Resilient and Elastic Members)

As stated above, a diaper with the crotch outer sheet 12M varies in elasticity among sections with different numbers of overlapping outer sheets, and therefore is prone to cause a bending phenomenon shown by an arrow in FIG. 20 particularly on the back side. Accordingly, to prevent this phenomenon, there are proposed arrangements in which resilient and elastic members 25 are fixed in an extended state in the absorber 20 in the front-back direction on the underside of the absorbent element, at least in an area ranging in the front-back direction from a site in the back end portion 22 to a site in the intermediate portion 23, as shown in FIGS. 11 to 16. By arranging the resilient and elastic members 25 in such a manner, an elastic force of the resilient and elastic members 25 acts on an area straddling an outer boundary BL so as to fit to the body of a wearer, thereby making the conventional bending phenomenon less prone to take place.

Although, in the illustrated arrangement, the resilient and elastic members 25 use elongated resilient and elastic members such as rubber threads, the resilient and elastic members 25 may also be wide, belt-like or net-like resilient and elastic members. Dimensions, extension ratio, layout and the like of the resilient and elastic members 25 can be appropriately decided so as to exert an effect of preventing the bending phenomenon in the present invention.

An area 25L in the front-back direction in which the resilient and elastic members 25 are provided (in other words, an area in the front-back direction which receives an elastic force of the resilient and elastic members 25), can be decided as appropriate. Preferably, with respect to the boundary BL between the intermediate portion 23 and the back end portion 22 in the absorber 20, the area 25L ranges from a position at 5 to 180 mm, preferably 10 to 90 mm toward the back end portion 22, to a position at 5 to 180 mm, preferably 10 to 90 mm toward the intermediate portion 23. Setting the area 25L excessively narrow in the front-back direction decreases the effect of preventing the bending phenomenon, and setting the area 25L excessively wide in the front-back direction produces the effect of preventing the bending phenomenon but leads unfavorably to appearance deterioration and cost increase.

In general, it is preferred that the resilient and elastic members 25 be provided in the area 25L ranging in the front-back direction from a position at 5 mm to a position at 180 mm on the back side, with reference to a center CL of the product in the front-back direction, and no resilient and elastic members be provided on the ventral side. In the illustrated example, when the resilient and elastic members 25 are sandwiched in the crotch outer sheet 12M, the resilient and elastic members 25 are preferably separated at the back-side ends from the back-side end of the crotch outer sheet 12M toward the crotch portion. A separation distance 25Y is preferably 5 mm or more.

The resilient and elastic members 25 may be arranged in any positions in the thickness direction so far as the resilient and elastic members 25 are positioned on the underside of the absorbent element 50. In the illustrated example, however, the resilient and elastic members 25 are provided only between the liquid impervious sheet 70 and the crotch outer sheet 12M. Although not shown, in a possible arrangement, the crotch outer sheet 12M is attached to the outsides of the ventral- and back-side outer sheets 12F and 12B, and the resilient and elastic members 25 are sandwiched at the intermediate portion 23 between the liquid impervious sheet 70 and the crotch outer sheet 12M, and sandwiched at the back end portion 22 between the back-side outer sheet and the crotch outer sheet 12M.

If elongated resilient and elastic members are used as the resilient and elastic members 25, positions thereof in the width direction can be decided as appropriate. Preferably, as in the illustrated example, the resilient and elastic members 25 are arranged in parallel in the front-back direction on the absorber 20 only at the central portion in the width direction and on the both sides in the width direction. In addition, when arranging the elongated resilient and elastic members 25 in three lines as stated above, rubber threads with a fineness of 470 to 1,000 dtex (for synthetic rubber. For natural rubber, about 0.1 to 1.0 $mm^2$, in cross-section area) are preferably fixed as the resilient and elastic members 25 at an extension ratio of 150 to 220% at intervals D of 10 to 100 mm, in particular 30 to 70 mm, in the width direction. If an elastic force of the resilient and elastic members 25 is insufficient, the bending phenomenon becomes prone to take place. If an elastic force of the resilient and elastic members 25 is excessively strong, the bending phenomenon in the reverse direction becomes prone to occur. The separation distance 25D between the resilient and elastic members 25 on the both sides in the width direction and the edges of the absorber 20 on the both sides in the width direction, is preferably 0 to 60 mm, particularly 10 to 40 mm.

Further, when arranging the elongated resilient and elastic members 25 in three lines as stated above, the extension ratio of the elongated resilient and elastic members 25 at the central portion in the width direction, is preferably in particular made higher than the extension ratio of the elongated resilient and elastic members 25 on the both sides in the width direction.

As shown in FIG. 17, the resilient and elastic members 25 may be provided in parallel in the front-back direction only on the both sides of the absorber 20 in the width direction. In this case, rubber threads with a fineness of 470 to 1,000 dtex (for synthetic rubber. For natural rubber, about 0.1 to 1.0 $mm^2$, in cross-section area) are preferably fixed as the resilient and elastic members 25 at the extension ratio of 150 to 220% at the intervals D of 20 to 180 mm, in particular 60 to 140 mm, in the width direction. In addition, the separation distance 25D between the resilient and elastic members 25 on the both sides in the width direction and the edges of the absorber 20 on the both sides in the width direction, is preferably 0 to 60 mm, in particular 10 to 40 mm.

(Method for Fixing the Resilient and Elastic Members by Sheet Welding)

The foregoing elongated resilient and elastic members (15, 16, 25 and others) may be fixed to adjacent sheets by an adhesive such as a hot-melt adhesive, or may be fixed by a method described below without lowering air permeability.

FIG. 18 shows a method for fixing elongated resilient and elastic members EL by a force of friction with sheets ST, ST for sandwiching the elongated resilient and elastic members EL. In the method, the sheets ST, ST are welded at predetermined intervals, with the elongated resilient and elastic members EL in a stretched state. In the diagram, reference numeral M denotes a welded portion, and reference numeral N a non-welded portion. With such an arrangement, the elongated resilient and elastic members EL can be firmly fixed without the use of an adhesive. In addition, since the elongated resilient and elastic members EL are not adhered, elastic sections can be formed with air permeability and softness. The welding may be ultrasonic welding or thermal welding. However, ultrasonic welding is more preferred because the sections near the elongated resilient and elastic members EL and the sheets ST, ST are less affected by heat and pressure resulting form ultrasonic welding than thermal welding.

In addition, FIG. 19 shows a method for fixing the elongated resilient and elastic members EL to the sheets ST, ST by a force of friction with the sheets ST, ST and a force of adhesion at the ends of the elongated resilient and elastic members EL in the width direction. In the method, the both ends of the elongated resilient and elastic members EL in the width direction are in a stretched state, and the elongated resilient and elastic members EL and the sheets ST, ST are welded together at predetermined intervals. In the diagram, reference numeral M denotes a welded portion, and reference numeral N a non-welded portion. With such an arrangement, the elongated resilient and elastic members EL can be more firmly fixed by a force of friction with the sheets ST, ST and a force of adhesion at the ends of the elongated resilient and elastic members EL in the width direction. Since the elongated resilient and elastic members EL are adhered only at the ends in the width direction, there is no fear that the elongated resilient and elastic members EL are deteriorated or cut off.

The elongated resilient and elastic members EL are fixed to the sheets ST, ST by a force of friction with the sheets ST, ST in such a manner that the elongated resilient and elastic members EL, in a stretched state, are intermittently welded at inner and outer layers near the both ends in the width direction, and the elongated resilient and elastic members EL are fixed to the sheets ST, ST. Accordingly, by removing load afterward (no tension), the elongated resilient and elastic members EL are increased in cross-section outer diameter, and a pressing force is applied to the elongated resilient and elastic members EL so as to be sandwiched in the sheets ST, ST at the welded portions on the both sides in the width direction. Therefore, the elongated resilient and elastic members EL do not need to be fixed with an adhesive, and the elongated resilient and elastic members EL can be fixed to the sheets ST, ST only by a force of friction with the sheets ST, ST.

INDUSTRIAL APPLICABILITY

The present invention is applicable to underpants type disposable diapers that are formed in advance in the shape of underpants.

Figure 1:
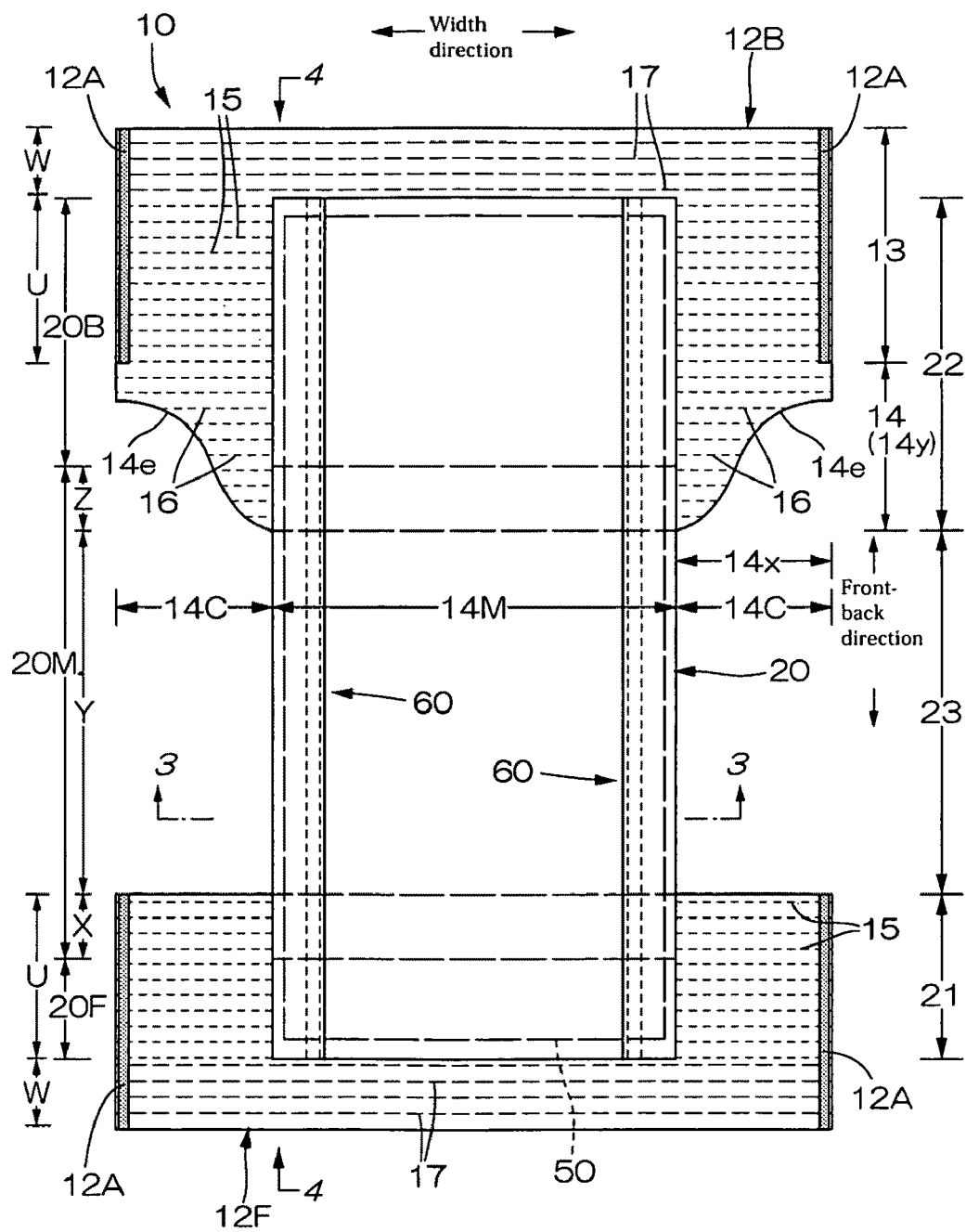
FIG. 1 is a plan view of an inner side of an embodiment in an open state.
Figure 2:
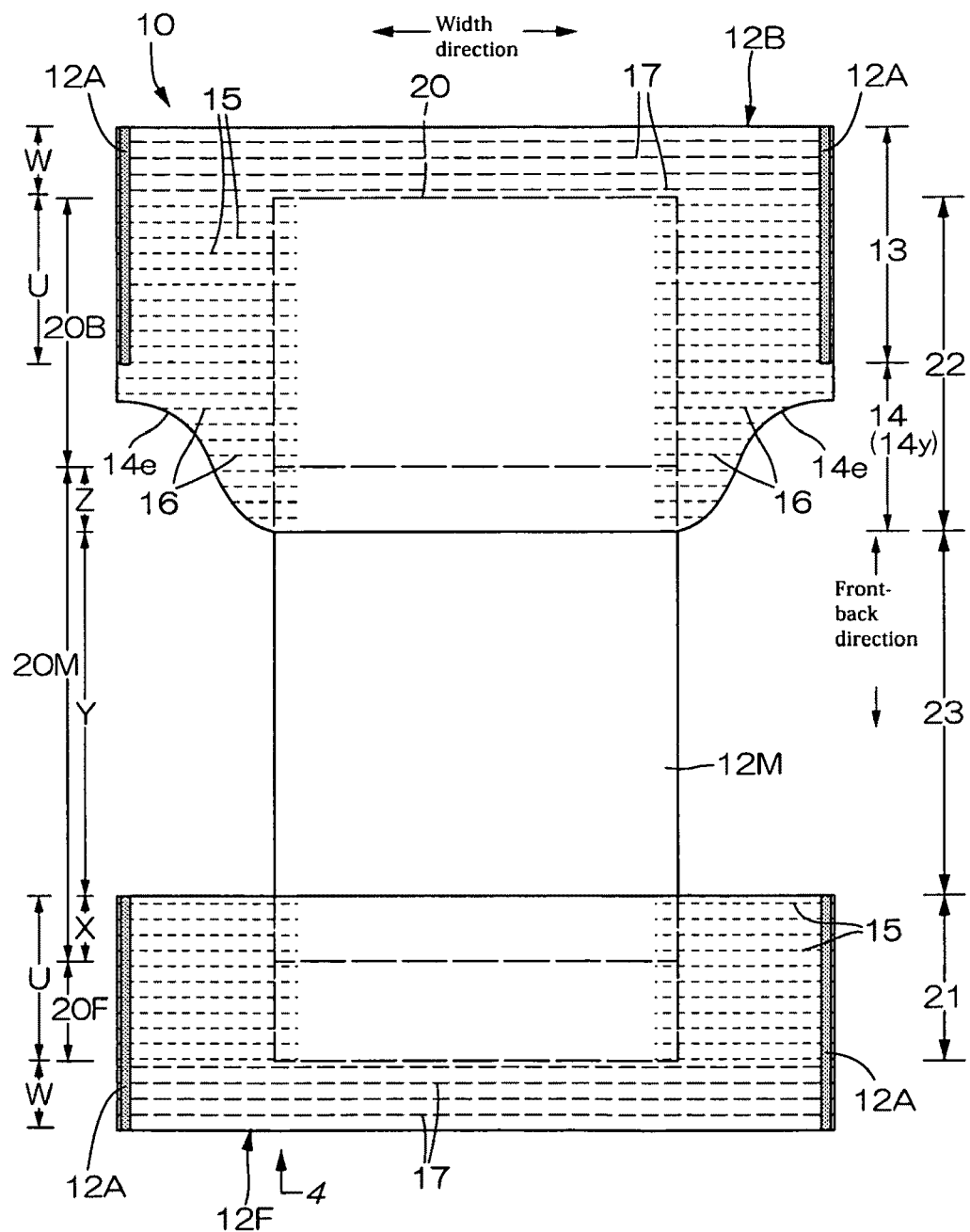
FIG. 2 is a plan view of an outer side of the embodiment in an open state.
Figure 3:
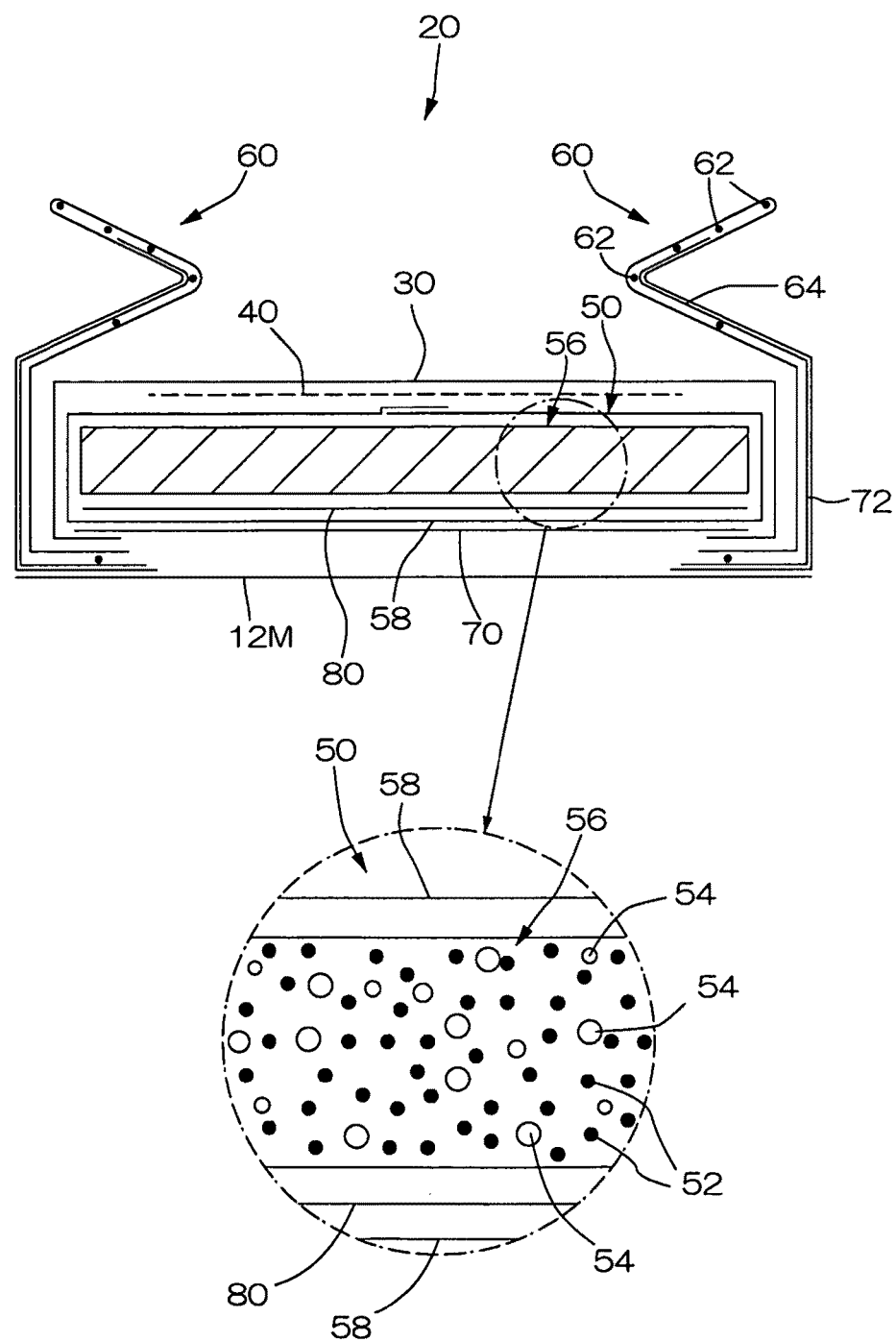
FIG. 3 is a cross-section view of FIG. 1 taken along line 3-3.
Figure 4:
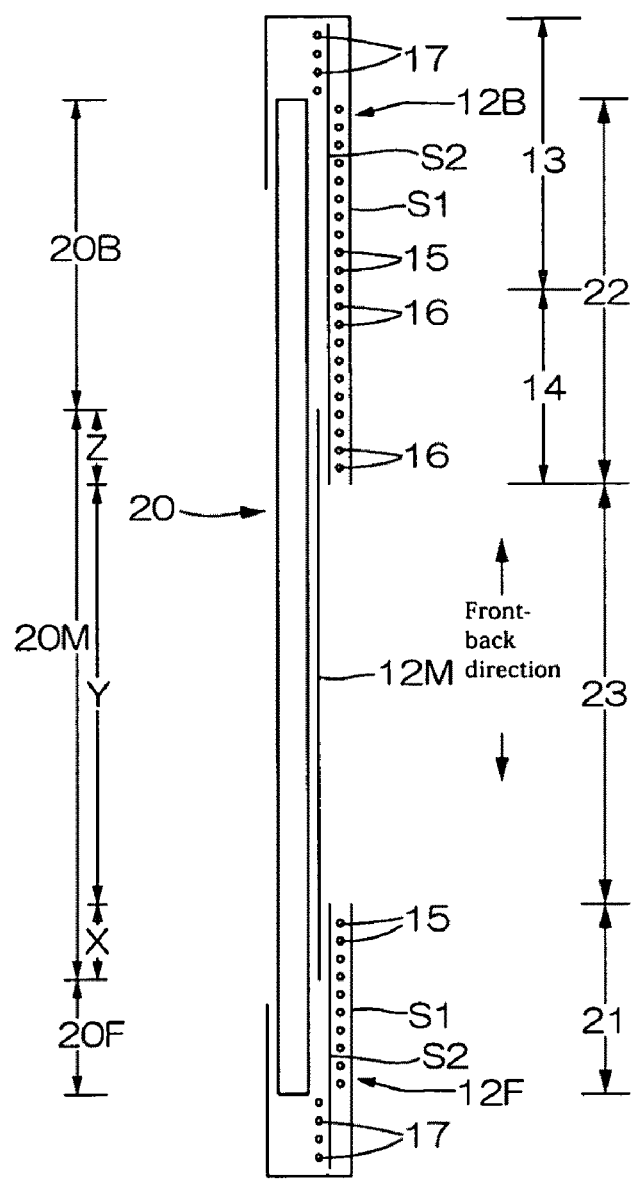
FIG. 4 is a cross-section view of FIG. 1 taken along line 4-4.
Figure 5:
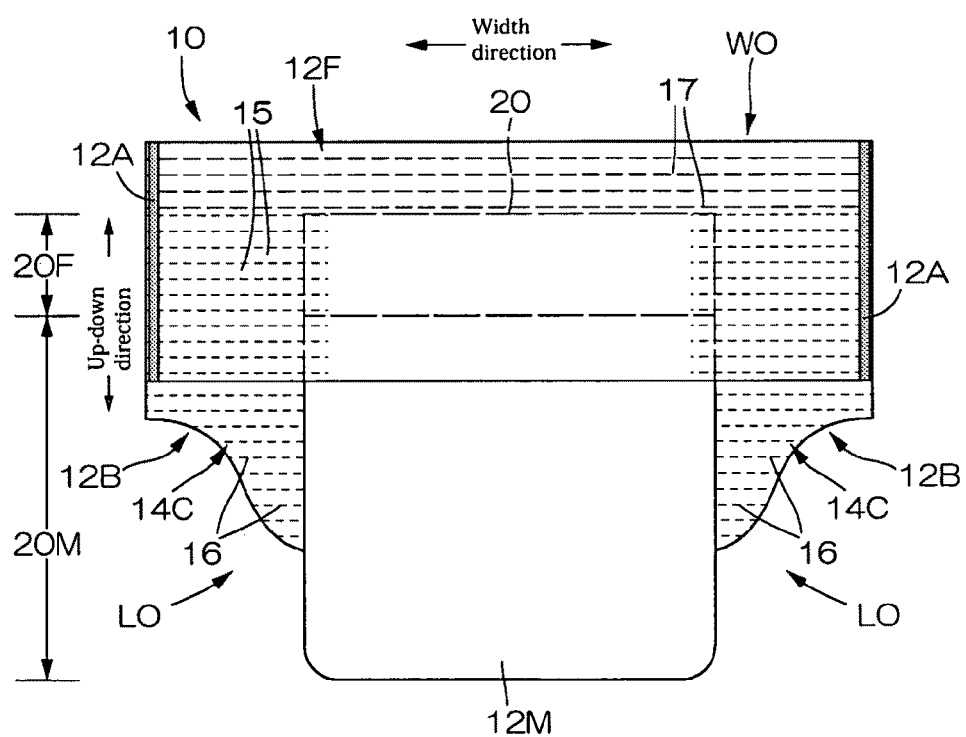
FIG. 5 is a front view of a product state.
Figure 6:
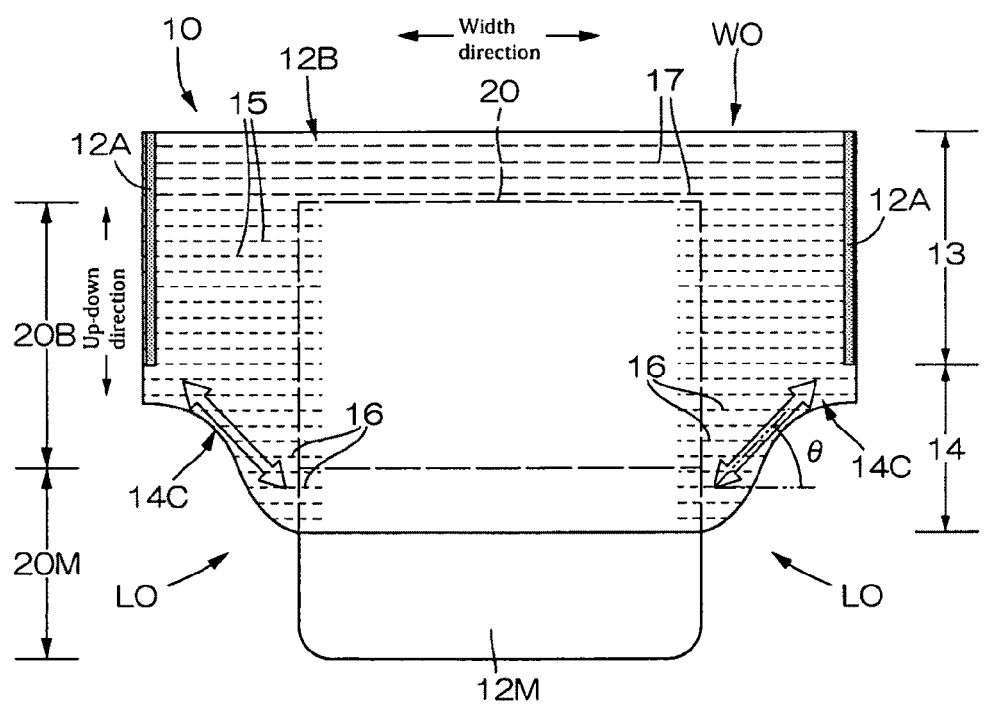
FIG. 6 is a rear view of the product state.
Figure 7:
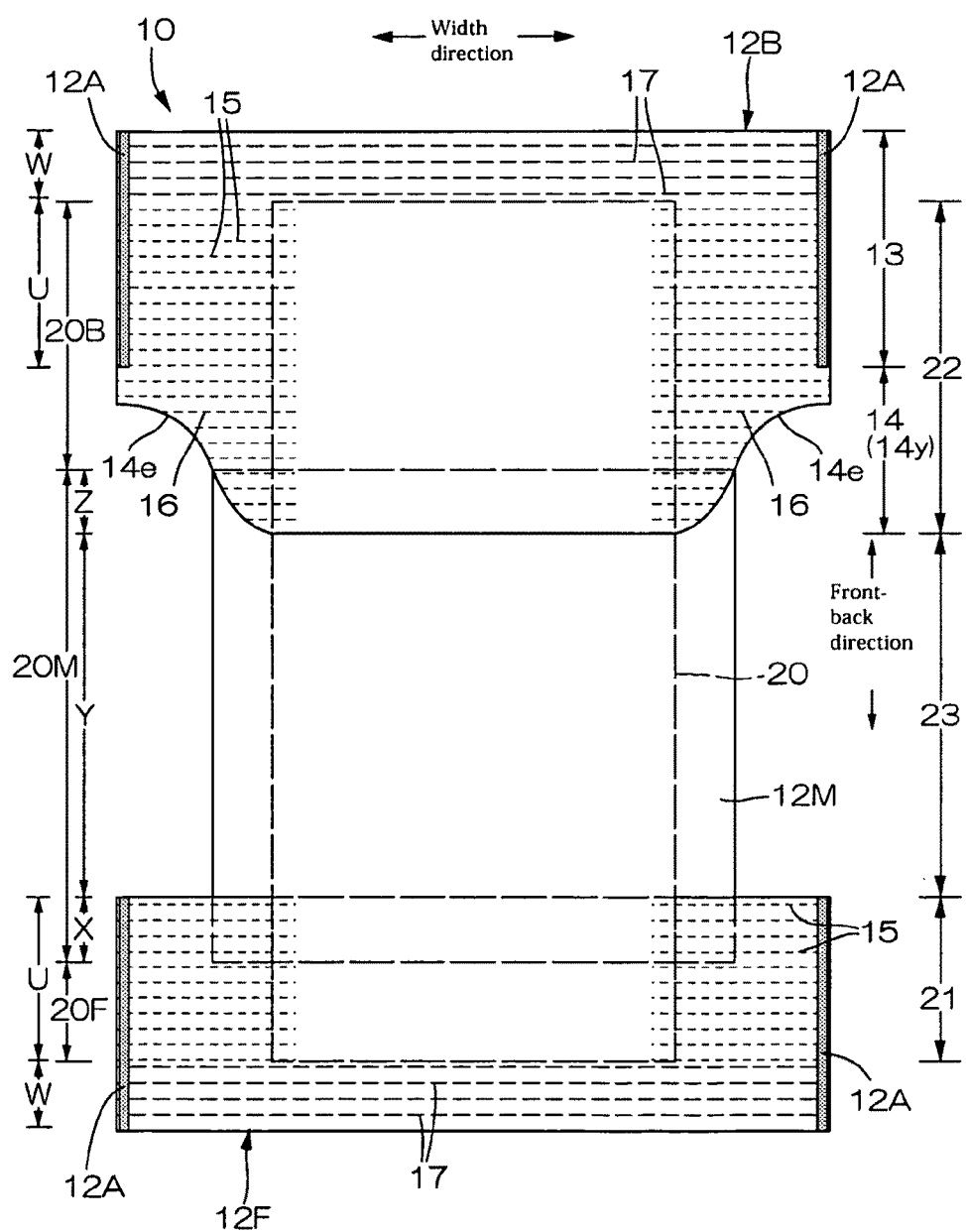
FIG. 7 is a plan view of an outer side of another embodiment in an open state.
Figure 8:
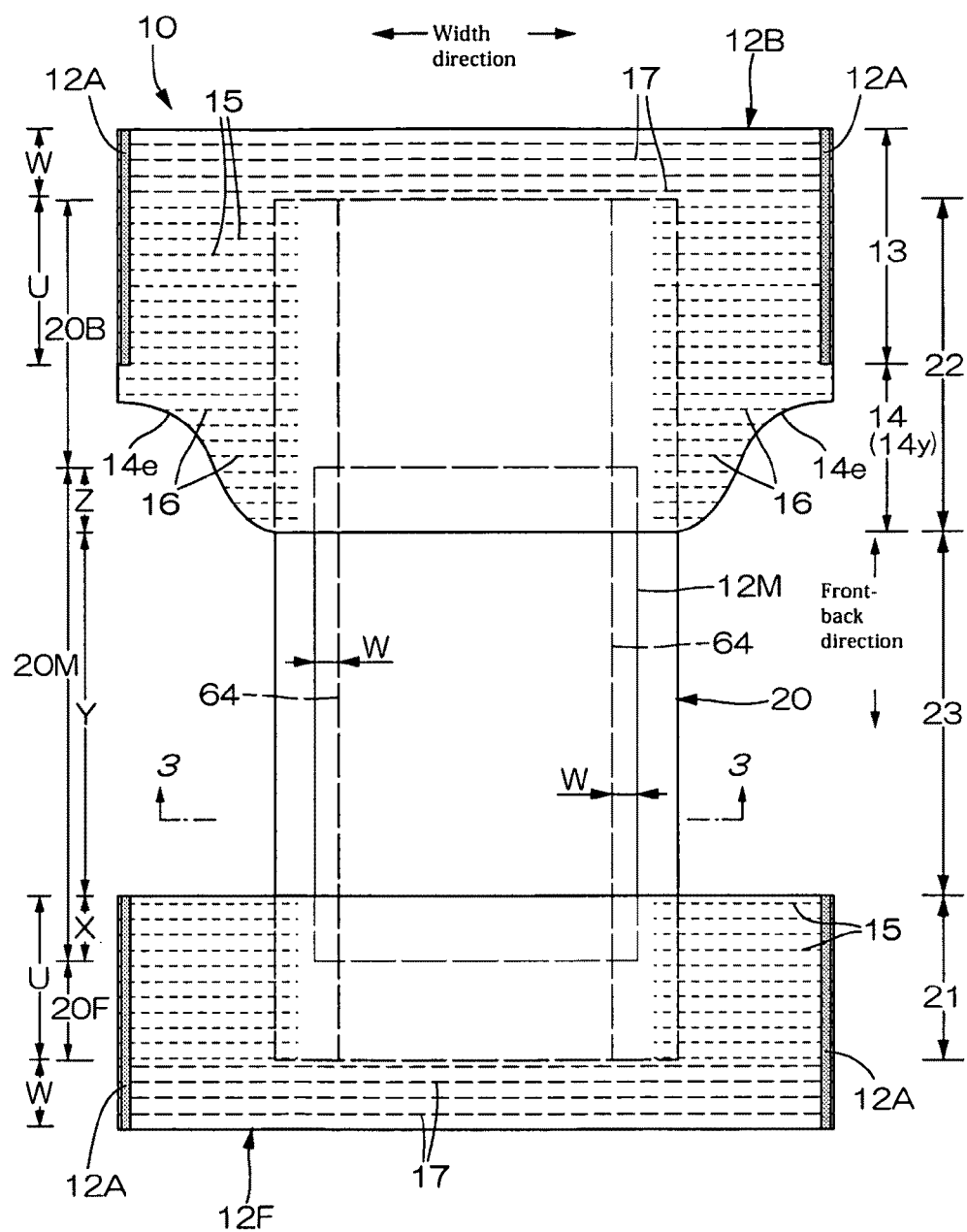
FIG. 8 is a plan view of an outer side of another embodiment in an open state.
Figure 9:
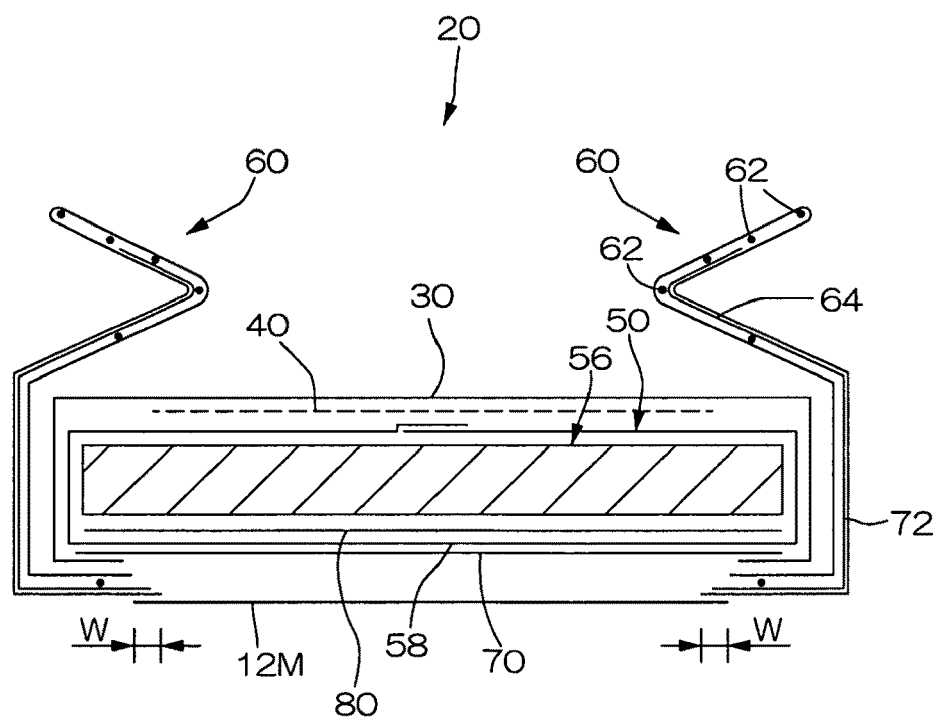
FIG. 9 is a cross-section view of FIG. 8 taken along line 9-9.
Figure 10:
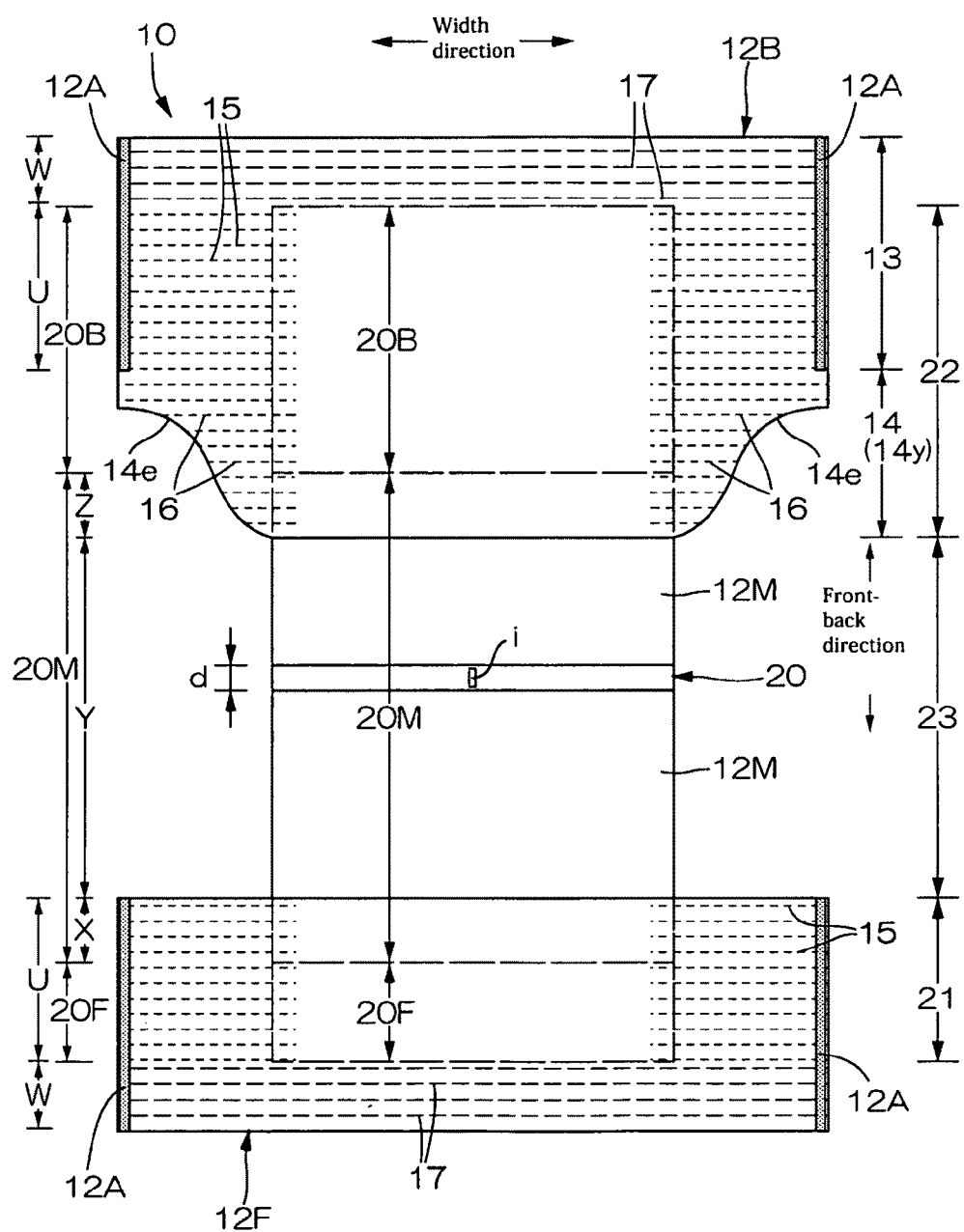
FIG. 10 is a plan view of an outer side of another embodiment in an open state.
Figure 11:
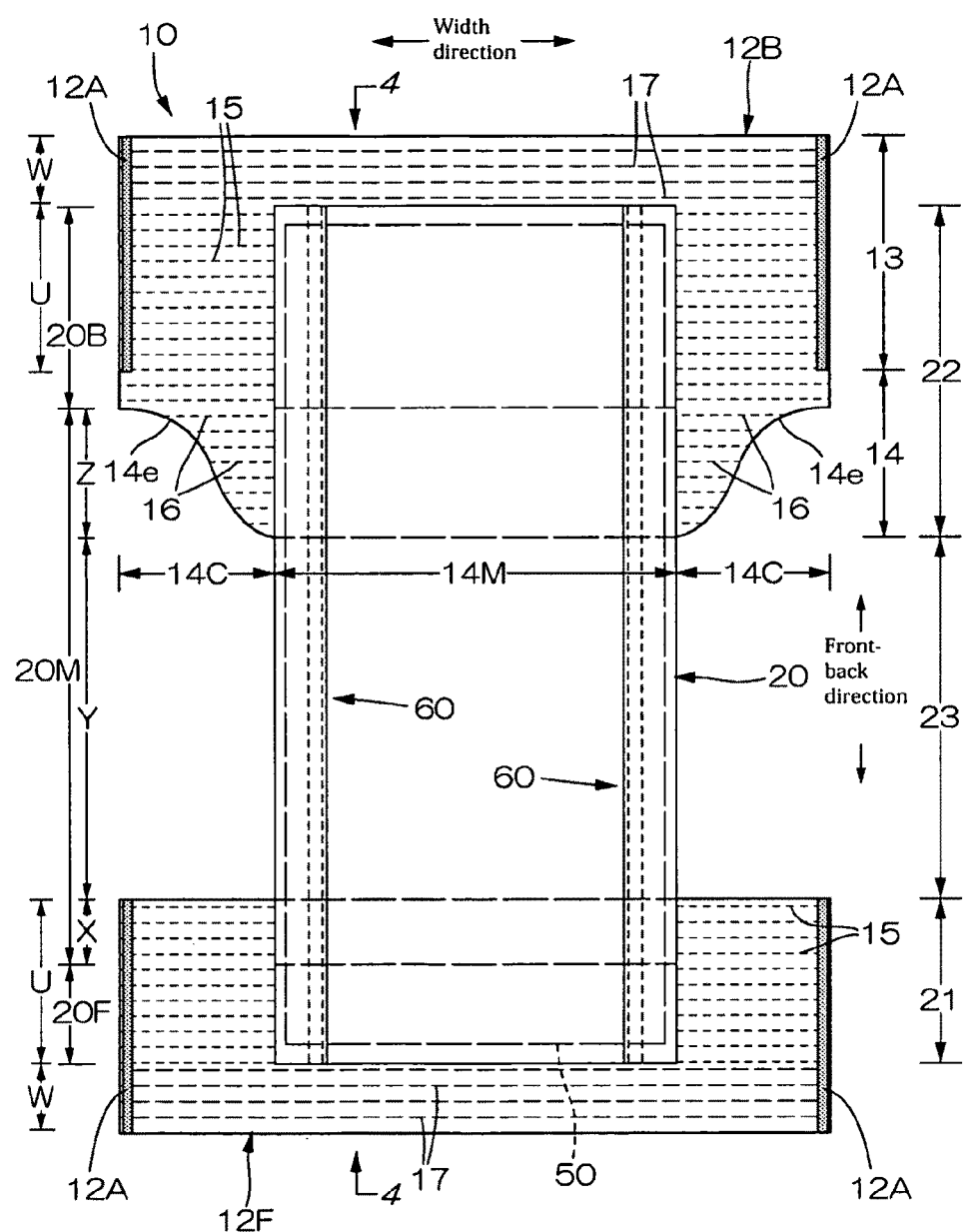
FIG. 11 is a plan view of an inner side of an embodiment in an open state.
Figure 12:
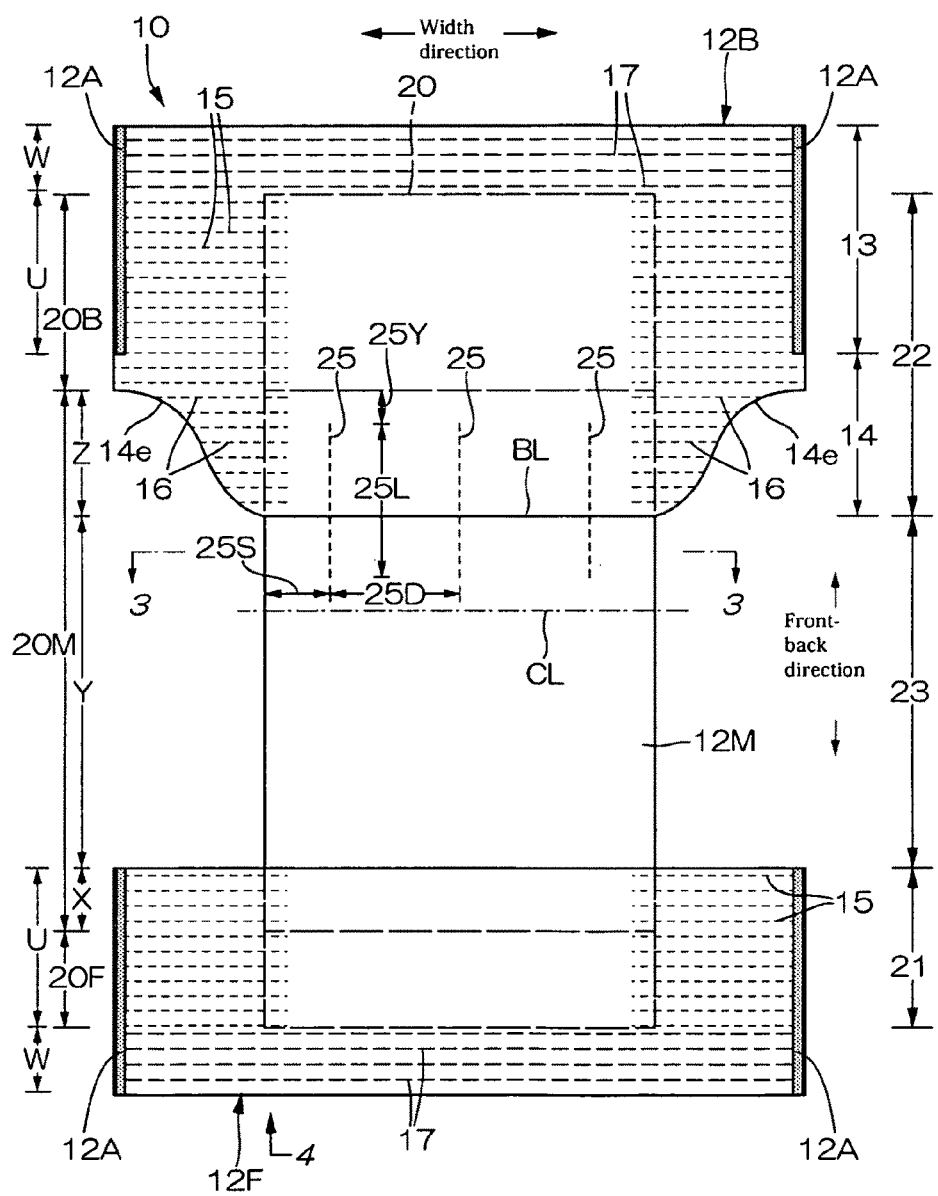
FIG. 12 is a plan view of an outer side of the embodiment in an open state.
Figure 13:
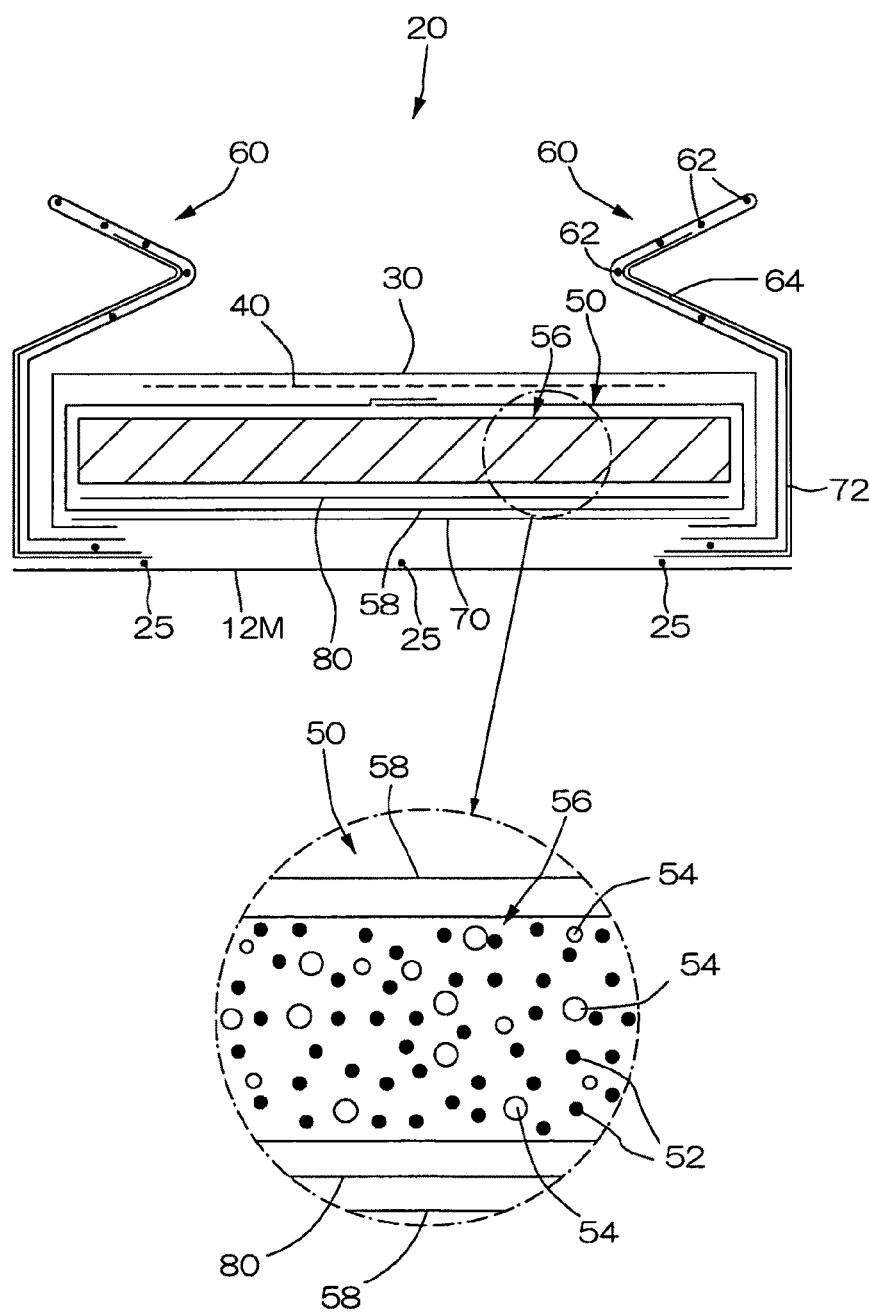
FIG. 13 is a cross-section view of FIG. 2 taken along line 3-3.
Figure 14:
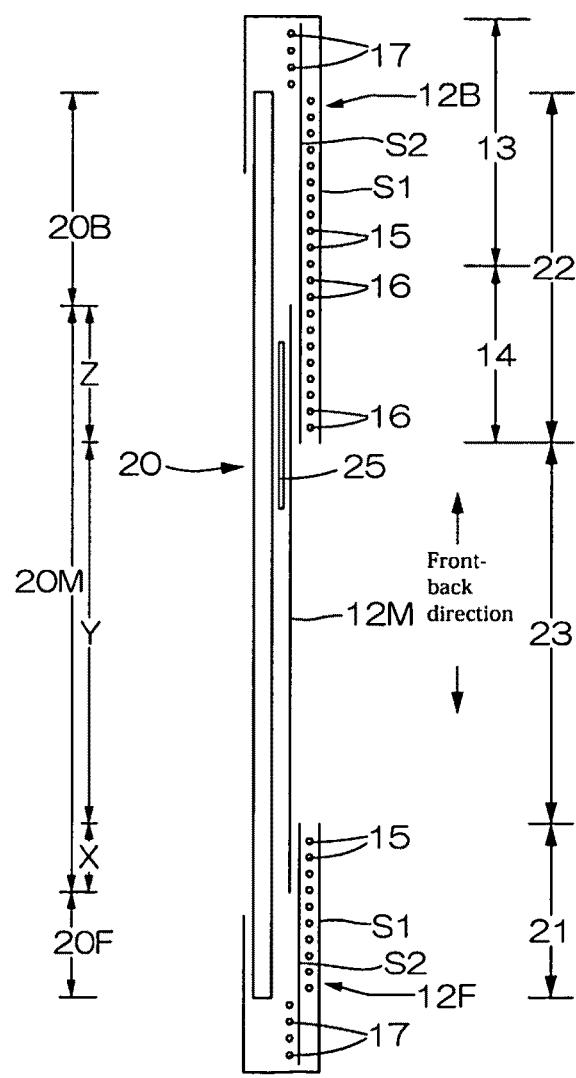
FIG. 14 is a cross-section view of FIG. 1 taken along line 4-4.
Figure 15:
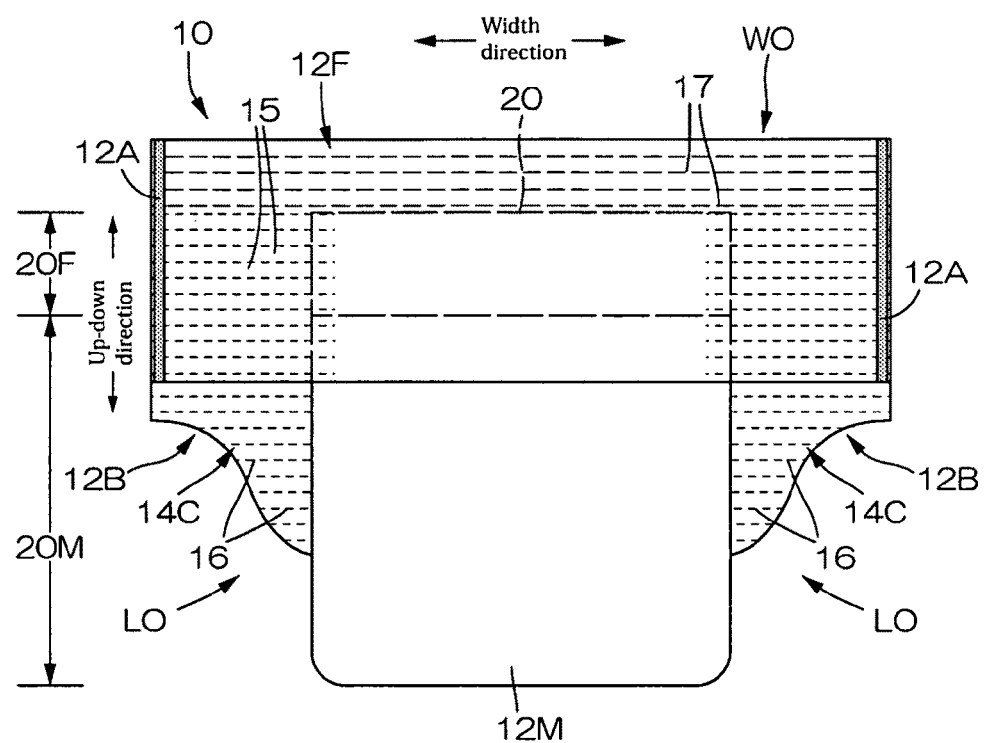
FIG. 15 is a front view of a product state.
Figure 16:
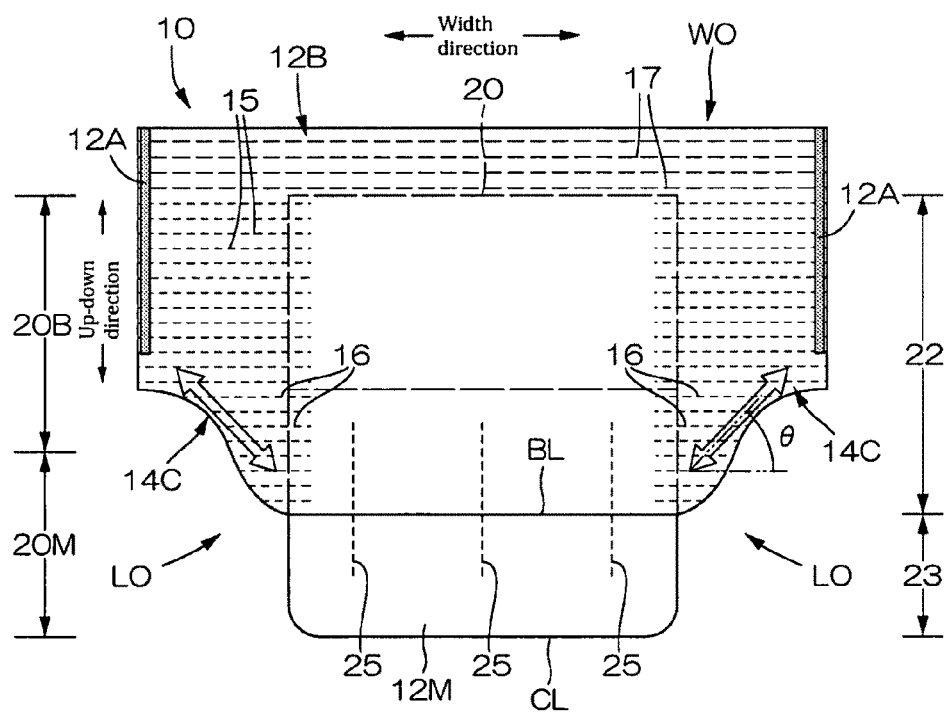
FIG. 16 is a rear view of the product state.
Figure 17:
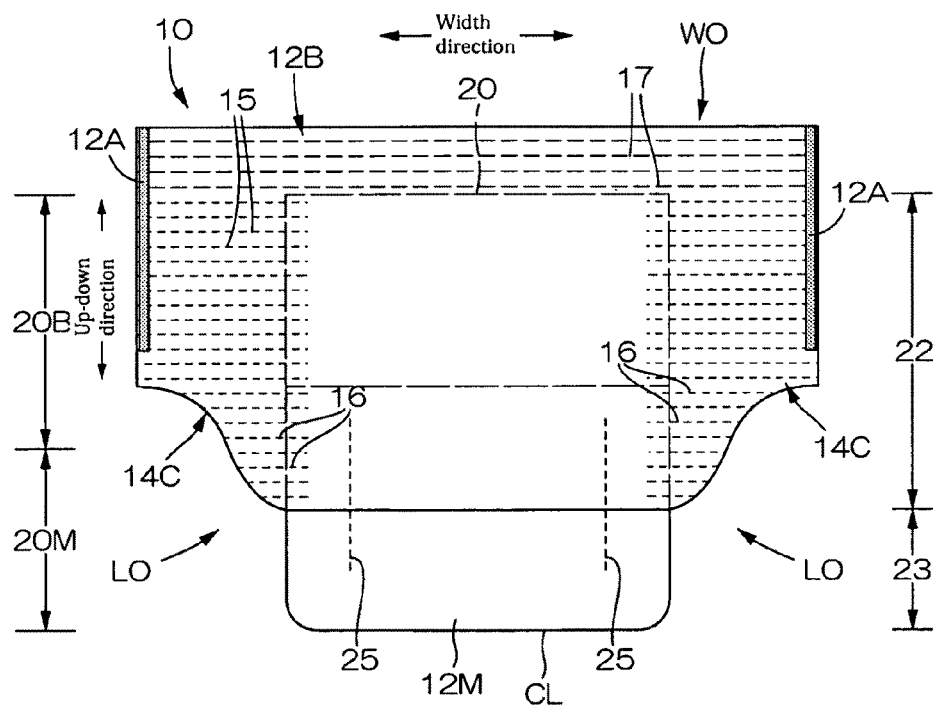
FIG. 17 is a rear view of another embodiment in a product state.
Figure 18:
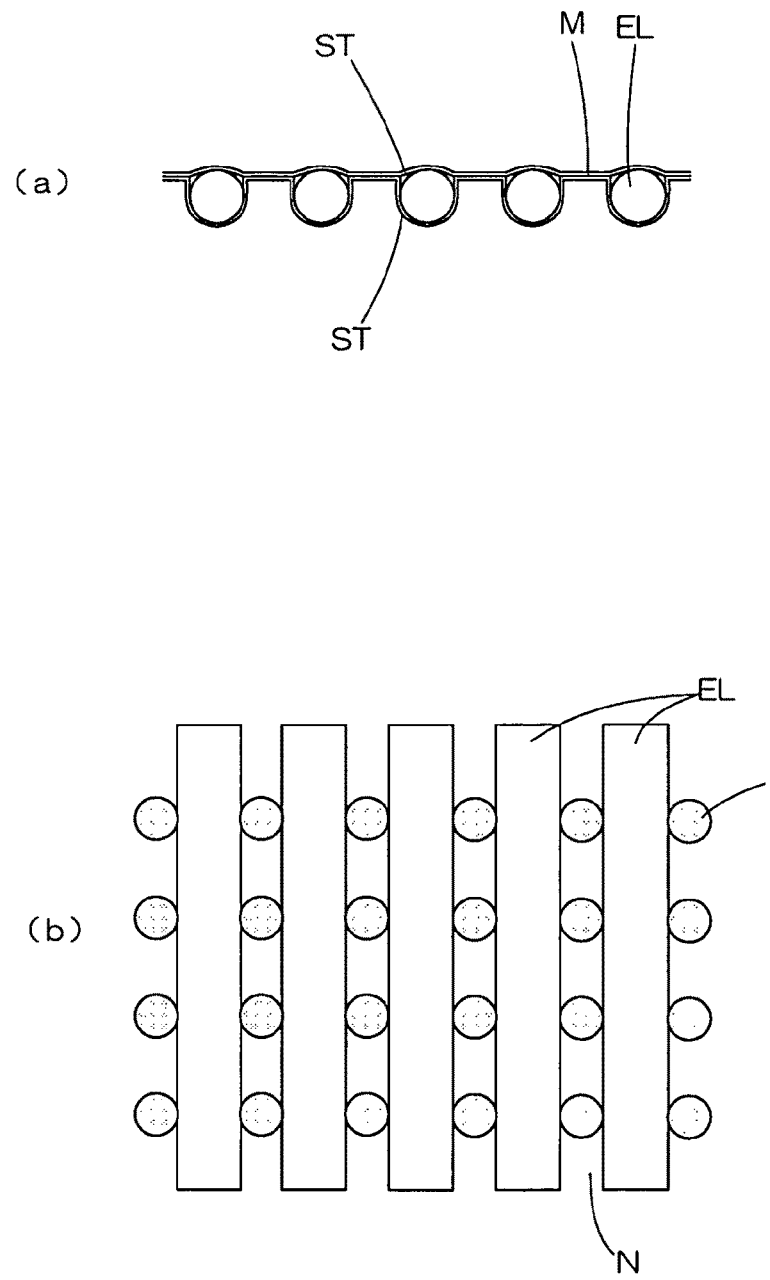
FIG. 18 is a schematic diagram showing a method for fixing resilient and elastic members by welding.
Figure 19:
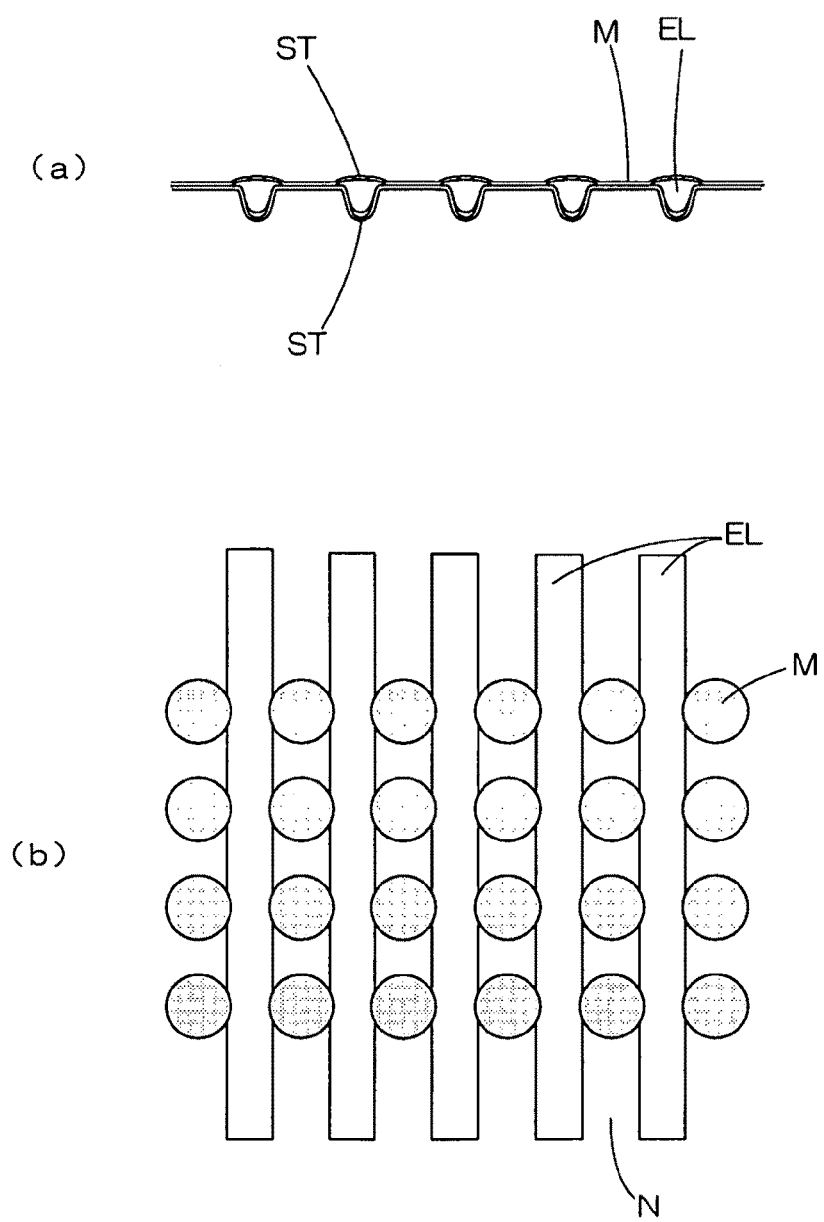
FIG. 19 is a schematic diagram showing a method for fixing resilient and elastic members by welding.
Figure 20:
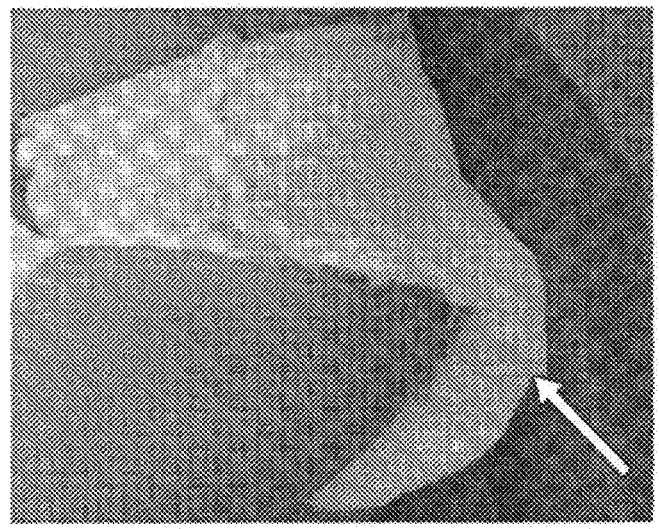
FIG. 20 is a photograph of a conventional diaper taken from a side.

20 .... Absorber, 12 .... Outer sheet, 12F .... Ventral-side outer sheet, 12B .... Back-side outer sheet, 12M .... Crotch outer sheet, 13 .... Main unit section, 14 .... Extension section, 15 .... First elongated resilient and elastic members, 16 .... Second elongated resilient and elastic members, 25 .... Elongated resilient and elastic members

The invention claimed is:
1. An underpants type disposable diaper, comprising:
a barrel-shaped waist portion that includes a ventral-side outer sheet for covering a waist of a wearer on a ventral side and a back-side outer sheet for covering a waist of a wearer on a back side, in which the ventral- and back-side outer sheets are joined together at joined sections at edges on the both sides in a width direction, and the ventral- and back-side outer sheets are not connected but separated at a crotch portion; and
an absorber that is connected at a front end portion to the ventral-side outer sheet on an inner surface at a central portion in the width direction and is connected at a back end portion to the back-side outer sheet on an inner surface at a central portion in the width direction, in which an intermediate portion between the front and back end portions is exposed to outside from a separation area between the ventral- and back-side outer sheets at the crotch portion, wherein
the absorber has a liquid pervious top sheet arranged on a top side, a liquid impervious sheet arranged on an underside, and an absorbent element interposed between the foregoing sheets to absorb and retain a liquid,
a crotch outer sheet is laminated on an underside of the liquid impervious sheet in the absorber so as to be exposed to on an external surface of a product,
the crotch outer sheet is higher in stiffness than sheets constituting the ventral- and back-side outer sheets,
the crotch outer sheet is disposed in an area ranging in a front-back direction from an intermediate position between the front end portion of the absorber and a crotch-side side edge of the ventral-side outer sheet to an intermediate position between the back end portion of the absorber and a crotch-side side edge of the back-side outer sheet,
the underpants type disposable diaper includes: a front-side outer nonoverlap section defined by an area ranging in the front-back direction from the front end portion of the absorber to the front end portion of the crotch outer sheet; a front-side outer overlap section in which the front end portion of the crotch outer sheet and the crotch-side side end of the ventral-side outer sheet overlap each other; a back-side outer nonoverlap section defined by an area in the front-back direction ranging from the back end portion of the absorber to the back end portion of the crotch outer sheet; and a back-side outer overlap section in which the back end portion of the crotch outer sheet and the crotch-side side end of the back-side outer sheet overlap each other,
assuming that the number of sheets constituting the outer sheets on the underside of the liquid impervious sheet is B1 at the intermediate portion, A1 at the front- and back-side outer overlap sections, and C1 at the front- and back-side outer nonoverlap sections, there is established a relationship of B1<C1<A1,
the ventral-side outer sheet and/or the back-side outer sheet have each a main unit section that constitutes an area identical in an up-down direction to the joined section, and an extension section that extends below the main unit section, and the overlap width of the front-side outer overlap section in the front-back direction and/or the overlap width of the back-side outer overlap section in the front-back direction are shorter than a length of the extension section in the front-back direction and are longer than ½ of the length of the extension section in the front-back direction, on each of the front and back sides.

2. The underpants type disposable diaper according to claim 1, wherein assuming that a basis weight of sheets constituting the outer sheets on the underside of the liquid impervious sheet is B2 at the intermediate portion, A2 at the front- and back-side outer overlap sections, and C2 at the front- and back-side outer nonoverlap sections, there is established a relationship of $B2<C2<A2$.

3. The underpants type disposable diaper according to claim 1, wherein the crotch outer sheet is formed in the same width as the absorber.

4. The underpants type disposable diaper according to claim 1, wherein the crotch outer sheet is formed wider than the absorber.

5. The underpants type disposable diaper according to claim 1, wherein the crotch outer sheet is formed narrower than the absorber.

6. The underpants type disposable diaper according to claim 1, wherein a plurality of crotch outer sheets is arranged at the intermediate portion at predetermined intervals.

7. The underpants type disposable diaper according to claim 6, wherein an indicator is provided to the absorber at least at a section without the crotch outer sheet so as to indicate absorption of a liquid.

8. An underpants type disposable diaper, comprising:
a barrel-shaped waist portion that includes a ventral-side outer sheet for covering a waist of a wearer on a ventral side and a back-side outer sheet for covering a waist of a wearer on a back side, in which the ventral- and back-side outer sheets are joined together at joined sections at edges on the both sides in a width direction, and the ventral- and back-side outer sheets are not connected but separated at a crotch portion; and
an absorber that is connected at a front end portion to the ventral-side outer sheet on an inner surface at a central portion in the width direction and is connected at a back end portion to the back-side outer sheet on an inner surface at a central portion in the width direction, in which an intermediate portion between the front and back end portions is exposed to outside from a separation area between the ventral- and back-side outer sheets at the crotch portion, wherein
the absorber has a liquid pervious top sheet arranged on a top side, a liquid impervious sheet arranged on an underside, and an absorbent element interposed between the foregoing sheets to absorb and retain a liquid,
a crotch outer sheet is laminated on an underside of the liquid impervious sheet in the absorber so as to be exposed to on an external surface of a product,
the crotch outer sheet is higher in stiffness than sheets constituting the ventral- and back-side outer sheets,
the crotch outer sheet is disposed in an area ranging in a front-back direction from an intermediate position between the front end portion of the absorber and a crotch-side side edge of the ventral-side outer sheet to an intermediate position between the back end portion of the absorber and a crotch-side side edge of the back-side outer sheet, the underpants type disposable diaper includes: a front-side outer nonoverlap section defined by an area ranging in the front-back direction from the front end portion of the absorber to the front end portion of the crotch outer sheet; a front-side outer overlap section in which the front end portion of the crotch outer sheet and the crotch-side side end of the ventral-side outer sheet overlap each other; a back-side outer nonoverlap section defined by an area in the front-back direction ranging from the back end portion of the absorber to the back end portion of the crotch outer sheet; and a back-side outer overlap section in which the back end portion of the crotch outer sheet and the crotch-side side end of the back-side outer sheet overlap each other, assuming that the number of sheets constituting the outer sheets on the underside of the liquid impervious sheet is B1 at the intermediate portion, A1 at the front- and back-side outer overlap sections, and C1 at the front- and back-side outer nonoverlap sections, there is established a relationship of $B1<C1<A1$, resilient and elastic members are fixed in an extended state in the absorber in the front-back direction on the underside of the absorbent element in the absorber, at least in an area ranging in the front-back direction from a site in the back end portion to a site in the intermediate portion, as the resilient and elastic members, elongated resilient and elastic members are provided in parallel in the front-back direction at the central and both side portions of the absorber in the width direction, and as the elongated resilient and elastic members, rubber threads with a fineness of 470 to 1,000 dtex are fixed at an extension rate of 150 to 220% in the width direction at intervals of 10 to 100 mm.

9. The underpants type disposable diaper according to claim 8, wherein the resilient and elastic members are provided between the liquid impervious sheet and the crotch outer sheet.

10. An underpants type disposable diaper, comprising:
a barrel-shaped waist portion that includes a ventral-side outer sheet for covering a waist of a wearer on a ventral side and a back-side outer sheet for covering a waist of a wearer on a back side, in which the ventral- and back-side outer sheets are joined together at joined sections at edges on the both sides in a width direction, and the ventral- and back-side outer sheets are not connected but separated at a crotch portion; and
an absorber that is connected at a front end portion to the ventral-side outer sheet on an inner surface at a central portion in the width direction and is connected at a back end portion to the back-side outer sheet on an inner surface at a central portion in the width direction, in which an intermediate portion between the front and back end portions is exposed to outside from a separation area between the ventral- and back-side outer sheets at the crotch portion, wherein
the absorber has a liquid pervious top sheet arranged on a top side, a liquid impervious sheet arranged on an underside, and an absorbent element interposed between the foregoing sheets to absorb and retain a liquid,
a crotch outer sheet is laminated on an underside of the liquid impervious sheet in the absorber so as to be exposed to on an external surface of a product,
the crotch outer sheet is higher in stiffness than sheets constituting the ventral- and back-side outer sheets,
the crotch outer sheet is disposed in an area ranging in a front-back direction from an intermediate position between the front end portion of the absorber and a crotch-side side edge of the ventral-side outer sheet to an intermediate position between the back end portion of the absorber and a crotch-side side edge of the back-side outer sheet, the underpants type disposable diaper includes: a front-side outer nonoverlap section defined by an area ranging in the front-back direction from the front end portion of the absorber to the front end portion of the crotch outer sheet; a front-side outer overlap section in which the front end portion of the crotch outer sheet and the crotch-side side end of the ventral-side outer sheet overlap each other; a back-side outer nonoverlap section defined by an area in the front-back direction ranging from the back end portion of the absorber to the back end portion of the crotch outer sheet; and a back-side outer overlap section in which the back end portion of the crotch outer sheet and the crotch-side side end of the back-side outer sheet overlap each other, assuming that the number of sheets constituting the outer sheets on the underside of the liquid impervious sheet is $B1$ at the intermediate portion, $A1$ at the front- and back-side outer overlap sections, and $C1$ at the front- and back-side outer nonoverlap sections, there is established a relationship of $B1 < C1 < A1$, resilient and elastic members are fixed in an extended state in the absorber in the front-back direction on the underside of the absorbent element in the absorber, at least in an area ranging in the front-back direction from a site in the back end portion to a site in the intermediate portion, as the resilient and elastic members, elongated resilient and elastic members are provided in parallel in the front-back direction at the central and both side portions of the absorber in the width direction, and the extension rate of the elongated resilient and elastic members provided at the central portion in the width direction is set higher than the extension rate of the elongated resilient and elastic members provided in the both side portions in the width direction.

11. An underpants type disposable diaper according, comprising:

a barrel-shaped waist portion that includes a ventral-side outer sheet for covering a waist of a wearer on a ventral side and a back-side outer sheet for covering a waist of a wearer on a back side, in which the ventral- and back-side outer sheets are joined together at joined sections at edges on the both sides in a width direction, and the ventral- and back-side outer sheets are not connected but separated at a crotch portion; and an absorber that is connected at a front end portion to the ventral-side outer sheet on an inner surface at a central portion in the width direction and is connected at a back end portion to the back-side outer sheet on an inner surface at a central portion in the width direction, in which an intermediate portion between the front and back end portions is exposed to outside from a separation area between the ventral- and back-side outer sheets at the crotch portion, wherein the absorber has a liquid pervious top sheet arranged on a top side, a liquid impervious sheet arranged on an underside, and an absorbent element interposed between the foregoing sheets to absorb and retain a liquid, a crotch outer sheet is laminated on an underside of the liquid impervious sheet in the absorber so as to be exposed to on an external surface of a product, the crotch outer sheet is higher in stiffness than sheets constituting the ventral- and back-side outer sheets, the crotch outer sheet is disposed in an area ranging in a front-back direction from an intermediate position between the front end portion of the absorber and a crotch-side side edge of the ventral-side outer sheet to an intermediate position between the back end portion of the absorber and a crotch-side side edge of the back-side outer sheet, the underpants type disposable diaper includes: a front-side outer nonoverlap section defined by an area ranging in the front-back direction from the front end portion of the absorber to the front end portion of the crotch outer sheet; a front-side outer overlap section in which the front end portion of the crotch outer sheet and the crotch-side side end of the ventral-side outer sheet overlap each other; a back-side outer nonoverlap section defined by an area in the front-back direction ranging from the back end portion of the absorber to the back end portion of the crotch outer sheet; and a back-side outer overlap section in which the back end portion of the crotch outer sheet and the crotch-side side end of the back-side outer sheet overlap each other, assuming that the number of sheets constituting the outer sheets on the underside of the liquid impervious sheet is $B1$ at the intermediate portion, $A1$ at the front- and back-side outer overlap sections, and $C1$ at the front- and back-side outer nonoverlap sections, there is established a relationship of $B1 < C1 < A1$, resilient and elastic members are fixed in an extended state in the absorber in the front-back direction on the underside of the absorbent element in the absorber, at least in an area ranging in the front-back direction from a site in the back end portion to a site in the intermediate portion, and the resilient and elastic members extend by 5 to 180 mm toward the back end portion of the absorber and extend by 5 to 180 mm toward the intermediate portion of the absorber, with reference to a boundary between the intermediate portion and the back end portion.

* * * * *